US007289106B2

(12) United States Patent
Bailey et al.

(10) Patent No.: US 7,289,106 B2
(45) Date of Patent: Oct. 30, 2007

(54) METHODS AND APPARATUS FOR PALPATION SIMULATION

(75) Inventors: David Bailey, Redwood City, CA (US); J. Michael Brown, Washington, DC (US); Robert Cohen, Kensington, MD (US); Richard L. Cunningham, Washington, DC (US); Robert B. Falk, Takoma Park, MD (US); Miguel A. Otaduy, Chapel Hill, NC (US); Victor Wu, Boyds, MD (US)

(73) Assignee: Immersion Medical, Inc., Gaithersburg, MD (US)

( * ) Notice: Subject to any disclaimer, the term of this patent is extended or adjusted under 35 U.S.C. 154(b) by 341 days.

(21) Appl. No.: 10/846,917

(22) Filed: May 17, 2004

(65) Prior Publication Data
US 2005/0219205 A1    Oct. 6, 2005

Related U.S. Application Data

(60) Provisional application No. 60/558,357, filed on Apr. 1, 2004.

(51) Int. Cl.
*G09G 5/08* (2006.01)

(52) U.S. Cl. ..................... 345/158; 345/156

(58) Field of Classification Search ............ 345/156, 345/158, 160–176, 905, 904, 157, 159, 178, 345/184; 434/262; 600/587
See application file for complete search history.

(56) References Cited

U.S. PATENT DOCUMENTS

| 2,972,140 | A | 2/1961 | Hirsch |
| 3,157,853 | A | 11/1964 | Hirsch |
| 3,220,121 | A | 11/1965 | Cutler |
| 3,497,668 | A | 2/1970 | Hirsch |
| 3,517,446 | A | 6/1970 | Corlyon et al. |
| 3,623,064 | A | 11/1971 | Kagan |
| 3,662,076 | A | 5/1972 | Gordon et al. |
| 3,902,687 | A | 9/1975 | Hightower |
| 3,903,614 | A | 9/1975 | Diamond et al. |
| 3,911,416 | A | 10/1975 | Feder |

(Continued)

FOREIGN PATENT DOCUMENTS

EP    0349086    1/1990

(Continued)

OTHER PUBLICATIONS

International Search Report for International Application No. PCT/US2005/011308, date mailed, Dec. 12, 2005.

(Continued)

*Primary Examiner*—Nitin I. Patel
(74) *Attorney, Agent, or Firm*—Thelen Reid Brown Raysman & Steiner LLP; David B. Ritchie

(57) ABSTRACT

An apparatus comprises a manipulandum, a housing, a sensor and an actuator. The housing has a palpation region spaced apart from the manipulandum. The sensor is coupled to the palpation region of the housing. The sensor is configured to send a signal based on a palpation of the palpation region of the housing. The actuator is coupled to the manipulandum. The actuator is configured to send haptic output to the manipulandum based on the signal.

17 Claims, 14 Drawing Sheets

U.S. PATENT DOCUMENTS

| | | | |
|---|---|---|---|
| 3,994,282 A | 11/1976 | Moulet | |
| 4,127,752 A | 11/1978 | Lowthorp | |
| 4,160,508 A | 7/1979 | Salisbury | |
| 4,236,325 A | 12/1980 | Hall et al. | |
| 4,262,549 A | 4/1981 | Schwellenbach | |
| 4,333,070 A | 6/1982 | Barnes | |
| 4,360,345 A | 11/1982 | Hon | |
| 4,464,117 A | 8/1984 | Foerst | |
| 4,484,191 A | 11/1984 | Vavra | |
| 4,513,235 A | 4/1985 | Acklam et al. | |
| 4,581,491 A | 4/1986 | Boothroyd | |
| 4,599,070 A | 7/1986 | Hladky et al. | |
| 4,708,656 A | 11/1987 | De Vries et al. | |
| 4,710,876 A | 12/1987 | Cline et al. | |
| 4,713,007 A | 12/1987 | Alban | |
| 4,794,392 A | 12/1988 | Selinko | |
| 4,823,634 A | 4/1989 | Culver | |
| 4,885,565 A | 12/1989 | Embach | |
| 4,891,764 A | 1/1990 | McIntosh | |
| 4,896,554 A | 1/1990 | Culver | |
| 4,930,770 A | 6/1990 | Baker | |
| 4,934,694 A | 6/1990 | McIntosh | |
| 4,982,618 A | 1/1991 | Culver | |
| 5,019,761 A | 5/1991 | Kraft | |
| 5,022,384 A | 6/1991 | Freels | |
| 5,022,407 A | 6/1991 | Horch et al. | |
| 5,035,242 A | 7/1991 | Franklin | |
| 5,038,089 A | 8/1991 | Szakaly | |
| 5,078,152 A | 1/1992 | Bond | |
| 5,165,897 A | 11/1992 | Johnson | |
| 5,175,459 A | 12/1992 | Danial et al. | |
| 5,186,695 A | 2/1993 | Mangseth et al. | |
| 5,212,473 A | 5/1993 | Louis | |
| 5,235,868 A | 8/1993 | Culver | |
| 5,240,417 A | 8/1993 | Smithson et al. | |
| 5,271,290 A | 12/1993 | Fischer | |
| 5,275,174 A | 1/1994 | Cook | |
| 5,283,970 A | 2/1994 | Aigner | |
| 5,299,810 A | 4/1994 | Pierce | |
| 5,309,140 A | 5/1994 | Everett | |
| 5,334,027 A | 8/1994 | Wherlock | |
| 5,351,677 A * | 10/1994 | Kami et al. | 600/109 |
| 5,396,895 A | 3/1995 | Takashima et al. | |
| 5,429,140 A * | 7/1995 | Burdea et al. | 600/587 |
| 5,436,622 A | 7/1995 | Gutman et al. | |
| 5,437,607 A | 8/1995 | Taylor | |
| 5,466,213 A | 11/1995 | Hogan | |
| 5,482,472 A | 1/1996 | Garoni et al. | |
| 5,547,382 A | 8/1996 | Yamasaki | |
| 5,575,761 A | 11/1996 | Hajianpour | |
| 5,690,582 A | 11/1997 | Ulrich et al. | |
| 5,704,791 A | 1/1998 | Gillio | |
| 5,766,016 A | 6/1998 | Sinclair | |
| 5,785,630 A | 7/1998 | Bobick et al. | |
| 5,833,633 A * | 11/1998 | Sarvazyan | 600/587 |
| 5,855,553 A * | 1/1999 | Tajima et al. | 600/407 |
| 5,928,138 A | 7/1999 | Knight et al. | |
| 5,957,694 A | 9/1999 | Bunch | |
| 5,971,767 A | 10/1999 | Kaufman et al. | |
| 5,984,880 A | 11/1999 | Lander et al. | |
| 6,007,342 A | 12/1999 | TjOlsen | |
| 6,077,082 A | 6/2000 | Gibson et al. | |
| 6,088,020 A | 7/2000 | Mor | |
| 6,111,577 A | 8/2000 | Zilles et al. | |
| 6,113,395 A | 9/2000 | Hon | |
| 6,126,450 A | 10/2000 | Mukai et al. | |
| 6,160,489 A | 12/2000 | Perry et al. | |
| 6,193,519 B1 | 2/2001 | Eggert et al. | |
| 6,193,653 B1 | 2/2001 | Evans et al. | |
| 6,256,011 B1 | 7/2001 | Culver | |
| 6,300,938 B1 | 10/2001 | Culver | |
| 6,422,941 B1 | 7/2002 | Thorner et al. | |
| 6,660,016 B2 | 12/2003 | Lindsay | |
| 6,697,044 B2 * | 2/2004 | Shahoian et al. | 345/156 |
| 6,697,748 B1 | 2/2004 | Rosenberg et al. | |
| 6,703,550 B2 * | 3/2004 | Chu | 84/609 |
| 6,705,871 B1 * | 3/2004 | Bevirt et al. | 434/262 |
| 6,810,281 B2 * | 10/2004 | Brock et al. | 600/427 |
| 2003/0016207 A1 * | 1/2003 | Tremblay et al. | 345/156 |
| 2003/0036714 A1 | 2/2003 | Kuth | |
| 2003/0045815 A1 | 3/2003 | Ombrellaro | |
| 2003/0130674 A1 | 7/2003 | Kashahara et al. | |
| 2004/0002045 A1 | 1/2004 | Wellman et al. | |
| 2004/0066369 A1 * | 4/2004 | Rosenberg | 345/156 |
| 2004/0126746 A1 * | 7/2004 | Toly | 434/262 |
| 2004/0164960 A1 * | 8/2004 | Jacobus et al. | 345/161 |
| 2004/0254771 A1 * | 12/2004 | Riener et al. | 703/7 |

FOREIGN PATENT DOCUMENTS

| | | | |
|---|---|---|---|
| EP | 0 980 037 | | 2/2000 |
| JP | H2-185278 | | 7/1990 |
| JP | H4-8381 | | 1/1992 |
| JP | H5-192449 | | 8/1993 |
| JP | 06-209902 | * | 8/1994 |
| JP | H7-24147 | | 1/1995 |
| WO | 97/19440 | | 5/1997 |
| WO | 01/18617 | | 3/2001 |

OTHER PUBLICATIONS

Baigrie, "Electric Control Loading—A Low Cost, High Performance Alternative," *Proceedings of Interservice/Industry Training Systems Conference*, pp. 247-254, Nov. 6-8, 1990.

Iwata, "Pen-based Haptic Virtual Environment," 0-7803-1363-1/93 IEEE, pp. 287-292, 1993.

Russo, "The Design and Implementation of a Three Degree of Freedom Force Output Joystick," MIT Libraries Archives, pp. 1-131, May 1990, archived Aug. 14, 1990.

Brooks et al., "Hand Controllers for Teleoperation—A State-of-the-Art Technology Survey and Evaluation," JPL Publication 85-11; NASA-CR-175890; N85-28559, pp. 1-84, Mar. 1, 1985.

Jones et al., "A perceptual analysis of stiffness," ISSN 0014-4819 Springer International (Springer-Verlag); *Experimental Brain Research*, vol. 79, No. 1, pp. 150-156, 1990.

Burdea et al., "Distributed Virtual Force Feedback, Lecture Notes for Workshop on Force Display in Virtual Environments and its Application to Robotic Teleoperation," *1993 IEEE International Conference on Robotics and Automation*, pp. 25-44, May 2, 1993.

Snow et al., "Model-X Force-Reflecting-Hand-Controller,"NT Control No. NPO-17851; JPL Case No. 7348, pp. 1-4, with 45 pages of attachments, Jun. 15, 1989.

Ouh-Young, "Force Display in Molecular Docking," Doctoral Dissertation, University of North Carolina at Chapel Hill, UMI Order No. 9034744, pp. 1-369, 1990.

Tadros, Control System Design for a Three Degree of Freedom Virtual Environment Simulator Using Motor/Brake Pair Actuators, *MIT Archive*, pp. 1-88, Feb. 1990, archived Aug. 13, 1990.

Caldwell et al., "Enhanced Tactile Feedback (Tele-Taction) Using a Multi-Functional Sensory System,"1050-4729/93, pp. 955-960, 1993.

Adelstein, "Design and Implementation of a Force Reflecting Manipulandum for Manual Control research," DSC-vol. 42, *Advances in Robotics*, pp. 1-2, 1992.

Gotow et al., "Controlled Impedance Test Apparatus for Studying Human Interpretation of Kinesthetic Feedback," WA11-11:00, pp. 332-337.

Stanley et al., "Computer Simulation of Interacting Dynamic Mechanical Systems Using Distributed Memory Parallel Processors," DSC-vol. 42, *Advances in Robotics*, pp. 55-61, ASME 1992.

Russo, "Controlling Dissipative Magnetic Particle Brakes in Force Reflective Devices," DSC-vol. 42, *Advances in Robotics*, pp. 63-70, ASME 1992.

Kontarinis et al., "Display of High-Frequency Tactile Information to Teleoperators," *Telemanipulator Technology and Space Telerobotics*, Won S. Kim, Editor, Proc. SPIE vol. 2057, pp. 40-50, Sep. 7-9, 1993.

Patrick et al., "Design and Testing of A Non-reactive, Fingertip, Tactile Display for Interaction with Remote Environments," *Cooperative Intelligent Robotics in Space*, Rui J. deFigueiredo et al., Editor, Proc. SPIE vol. 1387, pp. 215-222, 1990.

Adelstein, "A Virtual Environment System For The Study of Human Arm Tremor," *Ph.D. Dissertation*, Dept. of Mechanical Engineering, MIT, Jun. 1989, archived Mar. 13, 1990.

Bejczy, "Sensors, Controls, and Man-Machine Interface for Advanced Teleoperation," Science, vol. 208, No. 4450, pp. 1327-1335, 1980.

Bejczy et al., "Generalization of Bilateral Force-Reflecting Control of Manipulators," *Proceedings Of Fourth CISM-IFToMM*, Sep. 8-12, 1981.

McAffee, "Teleoperator Subsystem/Telerobot Demonsdtrator: Force Reflecting Hand Controller Equipment Manual," *JPL* D-5172, Jan. 1988.

Minsky, "Computational Haptics: The Sandpaper System for Synthesizing Texture for a Force-Feedback Display," *Ph.D. Dissertation*, MIT, Jun. 1995, archived Jul. 6, 1995.

Jacobsen et al., "High Performance, Dextrous Telerobotic Manipulator With Force Reflection," *Intervention/ROV '91 Conference & Exposition*, Hollywood, Flordia, May 21-23, 1991.

Shimoga, "Finger Force and Touch Feedback Issues in Dexterous Telemanipulation," *Proceedings of Fourth Annual Conference on Intelligent Robotic Systems for Space Exploration*, Rensselaer Polytechnic Institute, Sep. 30-Oct. 1, 1992.

IBM Technical Disclosure Bulletin, "Mouse Ball-Actuating Device With Force and Tactile Feedback," vol. 32, No. 9B, Feb. 1990.

Terry et al., "Tactile Feedback In A Computer Mouse," *Proceedings of Fouteenth Annual Northeast Bioengineering Conference*, University of New Hampshire, Mar. 10-11, 1988.

Howe, "A Force-Reflecting Teleoperated Hand System for the Study of Tactile Sensing in Precision Manipulation," *Proceedings of the 1992 IEEE International Conference on Robotics and Automation*, Nice, France, May 1992.

Eberhardt et al., "OMAR—A Haptic display for speech perception by deaf and deaf-blind individuals," *IEEE Virtual Reality Annual International Symposium*, Seattle, WA, Sep. 18-22, 1993.

Rabinowitz et al., "Multidimensional tactile displays: Identification of vibratory intensity, frequency, and contactor area," *Journal of The Acoustical Society of America*, vol. 82, No. 4, Oct. 1987.

Bejczy et al., "Kinesthetic Coupling Between Operator and Remote Manipulator," *International Computer Technology Conference, The American Society of Mechanical Engineers*, San Francisco, CA, Aug. 12-15, 1980.

Bejczy et al., "A Laboratory Breadboard System For Dual-Arm Teleoperation," *SOAR '89 Workshop*, JSC, Houston, TX, Jul. 25-27, 1989.

Ouh-Young, "A Low-Cost Force Feedback Joystick and Its Use in PC Video Games," *IEEE Transactions on Consumer Electronics*, vol. 41, No. 3, Aug. 1995.

Marcus, "Touch Feedback in Surgery," *Proceedings of Virtual Reality and Medicine The Cutting Edge*, Sep. 8-11, 1994.

Bejczy, et al., "Universal Computer Control System (UCCS) For Space Telerobots," CH2413-3/87/0000/0318501.00 1987 IEEE, 1987.

Patrick, "Design, Construction, and Testing of a Fingertip Tactile Display for Interaction with Virtual and Remote Environments," *Master of Science Thesis*, MIT, Aug. 1990, archived Nov. 8, 1990.

Calder, "Design of A Force-Feedback Touch-Introducing Actuator For Teleoperator Robot Control," *Bachelor of Science Thesis*, MIT, May 1983, archived Jun. 23, 1983.

Wiker, "Teletouch Display Development: Phase 1 Report," *Technical Report 1230*, Naval Ocean Systems Center, San Diego, Jul. 1988.

Bliss, "Optical-to-Tactile Image Conversion for the Blind," *IEEE Transactions on Man-Machine Systems*, vol. MMS-11, No. 1, Mar. 1970.

Johnson, "Shape-Memory Alloy Tactile Feedback Actuator," *Armstrong Aerospace Medical Research Laboratory*, AAMRL-TR-90-039, Aug. 1990.

Kontarinis et al., "Tactile Display of Vibratory Information in Teleoperation and Virtual Environments," PRESENCE, 4(4):387-402, Harvard Univ., 1995.

Aukstakalnis et al., "Silicon Mirage: The Art and Science of Virtual Reality," ISBN 0-938151-82-7, pp. 129-180, 1992.

Eberhardt et al., "Inducing Dynamic Haptic Perception by The Hand: System Description and Some Results," DSC-vol. 55-1, *Dynamic Systems and Control*: vol. 1, ASME 1994.

Gobel et al., "Tactile Feedback Applied to Computer Mice," *International Journal of Human-Computer Interaction*, vol. 7, No. 1, pp. 1-24, 1995.

Pimentel et al., "Virtual Reality: through the new looking glass," 2nd Edition; McGraw-Hill, ISBN 0-07-050167-X, pp. 41-202, 1994.

"Cyberman Technical Specification," *Logitech Cyberman SWIFT Supplement to Logitech Mouse Technical Reference and Programming Guide*, Apr. 5, 1994.

Ouhyoung et al., "The Development of A Low-Cost Force Feedback Joystick and Its Use in the Virtual Reality Environment," *Proceedings of the Third Pacific Conference on Computer Graphics and Applications, Pacific Graphics '95*, Seoul, Korea, Aug. 21-24, 1995.

Kaczmarek et al., "Tactile Displays," *Virtual Environment Technologies*, Chap. 9, pp. 349-414.

Lake, "Cyberman from Logitech," at http://www.ibiblio.org/GameBytes/issue21/greviews/cyberman.html, 1994.

"Component Maintenance Manual With Illustrated Parts List, Coaxial Control Shaker Part No. C-25502," Safe Flight Instrument Corporation, Revised Jan. 28, 2002 (3 pages).

"Technical Manual Overhaul Instructions With Parts Breakdown, Coaxial Control Shaker Part No. C-25502," Safe Flight Instrument Corporation, Revised Jul. 15, 1980 (23 pages).

Scannell, "Taking a Joystick Ride," *Computer Currents*, Boston Edition, vol. 9, No. 11, Nov. 1994.

Yamakita et al., "Tele-Virtual Reality of Dynamic Mechanical Model," *Proceedings of the 1992 IEEE/RSJ International Conference on Intelligent Robots and Systems*, Raleigh, NC, Jul. 7-10, 1992.

Noll, "Man-Machine Tactile," *SID Journal*, Jul./Aug. 1972 Issue.

Rosenberg, "Virtual Fixtures: Perceptual Overlays Enhance Operator Performance in Telepresence Tasks," *Ph.D. Dissertation*, Stanford University, Jun. 1994.

Kuhnapfel et al., "Models for simulating instrument-tissue interactions," MMVR 2001, Newport Beach, Jan. 27, 2001.

Peine, "Remote Palpation Instruments for Minimally Invasive Surgery," http://www.hrl.harvard.edu/~peine/rpi.html.

Interlink Electronics, FSR Force Sensing Resistor, FSR Integration Guide and Evaluation Parts Catalog, Version 1.0, Camarillo, CA, pp. 1-26.

ITW FASTEX, Access Panel Fastener Lock—Tree-Lok Fastener, Des Plaines, IL, Copyright 2002-2004, printed on Apr. 30, 2004.

Interlink Electronics, FSR Force Sensing Resister Brochure, Copyright 2000.

* cited by examiner

METHODS AND APPARATUS FOR PALPATION SIMULATION

CROSS-REFERENCE TO RELATED APPLICATION

This application claims priority to U.S. patent application Ser. No. 60/558,357, entitled "Methods and Apparatus for Palpation Simulation," filed on Apr. 1, 2004, the entirety of which is incorporated herein by reference. This application is also related to U.S. application Ser. No. 09/848,966 (Publication No. US 2002/0163497 A1), entitled "Haptic Interface for Palpation Simulation," the entirety of which is incorporated herein by reference.

BACKGROUND

1. Field of the Invention

The present invention relates generally to simulation systems and methods, and more particularly to a system and method for using haptic feedback in a medical simulation involving, for example, both a simulated medical device and palpation of simulated tissue.

2. Discussion of the Background

Many medical procedures involve both the use of a medical device and the palpation of the patient by the medical practitioner. In such a medical procedure, for example, the medical practitioner can control the medical device with one hand while palpating the patient with the other hand. In other words, the medical device can be disposed on or partially within the patient and controlled with one hand of the medical practitioner while the medical practitioner coordinates palpation of an exterior area of the patient with the medical practitioner's other hand.

One such medical procedure, for example, relates to vein harvesting. In a procedure for minimally invasive vein harvesting (MIVH), an endoscopic tool is used to harvest the saphenous vein from a patient's leg. This harvested saphenous vein then can be used to create bypass grafts in coronary artery bypass graft (CABG) surgery. This harvesting procedure typically includes several steps. First, an incision near the knee is created. Then, using a conically tipped rigid endoscopic device (also referred to as a "dissector"), the saphenous vein is separated from surrounding fat and other tissue. Then, a capture and electrocautery device (also referred to as a "harvester") is used to capture the saphenous vein and to manipulate the saphenous vein so that side branches are exposed and pulled taut in position for cutting. The electrocautery device is then manipulated to cut and cauterize vein branches. The saphenous vein is then ligated at each end and removed from the leg through the small incision.

Due to the complexity of such medical procedures, a medical practitioner typically seeks training to obtain an acceptable level of proficiency. Such training previously has been performed on, for example, human cadavers. Training on human cadavers, however, has several drawbacks including cost, difficulty with storage, etc. Consequently, a need exists for systems and methods for simulating medical procedures where the medical practitioner can simulate the control of a medical device with one hand while palpating a simulated patient with the other hand.

SUMMARY OF THE INVENTION

An apparatus comprises a manipulandum, a housing, a sensor and an actuator. The housing has a palpation region spaced apart from the manipulandum. The sensor is coupled to the palpation region of the housing. The sensor is configured to send a signal based on a palpation of the palpation region of the housing. The actuator is coupled to the manipulandum. The actuator is configured to send haptic output to the manipulandum based on the signal.

DETAILED DESCRIPTION

In one embodiment, a simulation system comprises a manipulandum, a housing, a sensor and an actuator. The housing has a palpation region spaced apart from the manipulandum. The sensor is coupled to the palpation region of the housing. The sensor is configured to send a signal based on a palpation of the palpation region of the housing. The actuator is coupled to the manipulandum. The actuator is configured to send haptic output to the manipulandum based on the signal.

In an alternative embodiment, the manipulandum has a first portion external to the housing and a second portion internal to the housing. The second portion of the manipulandum is spaced apart from the palpation region of the housing and is moveable such that a force is translated to the palpation region of the housing when the manipulandum is moved.

Such embodiments can be used, for example, to simulate medical procedures. For example, many medical procedures require the medical practitioner to hold a medical device with one hand and simultaneously palpate the patient with the other hand. Such medical procedures can be simulated through a simulation system that senses the movements of the medical practitioner while providing haptic feedback. For example, a simulation system can sense the movement of the medical device (or simulated medical device) held in one hand of the medical practitioner while providing haptic feedback to the medical practitioner's other hand that is palpating a region of the patient and/or to the medical device held by the medical practitioner. Alternatively, the simulation system can sense the movement of the medical practitioner's one hand that is palpating a region of the patient while providing haptic feedback to the medical device (or simulated medical device) held in the other hand of the medical practitioner and/or to the medical practitioner's hand that is palpating a region of the patient.

In one such medical procedure, minimally invasive vein harvesting (MIVH), for example, the medical practitioner uses an endoscopic tool in one hand while palpating the patient's leg with the other hand to harvest the saphenous vein from the patient's leg. Although some of the embodiments disclosed herein are described in reference to an MIVH procedure, the embodiments can be adapted for any type of appropriate procedure or simulation.

Figure 1:
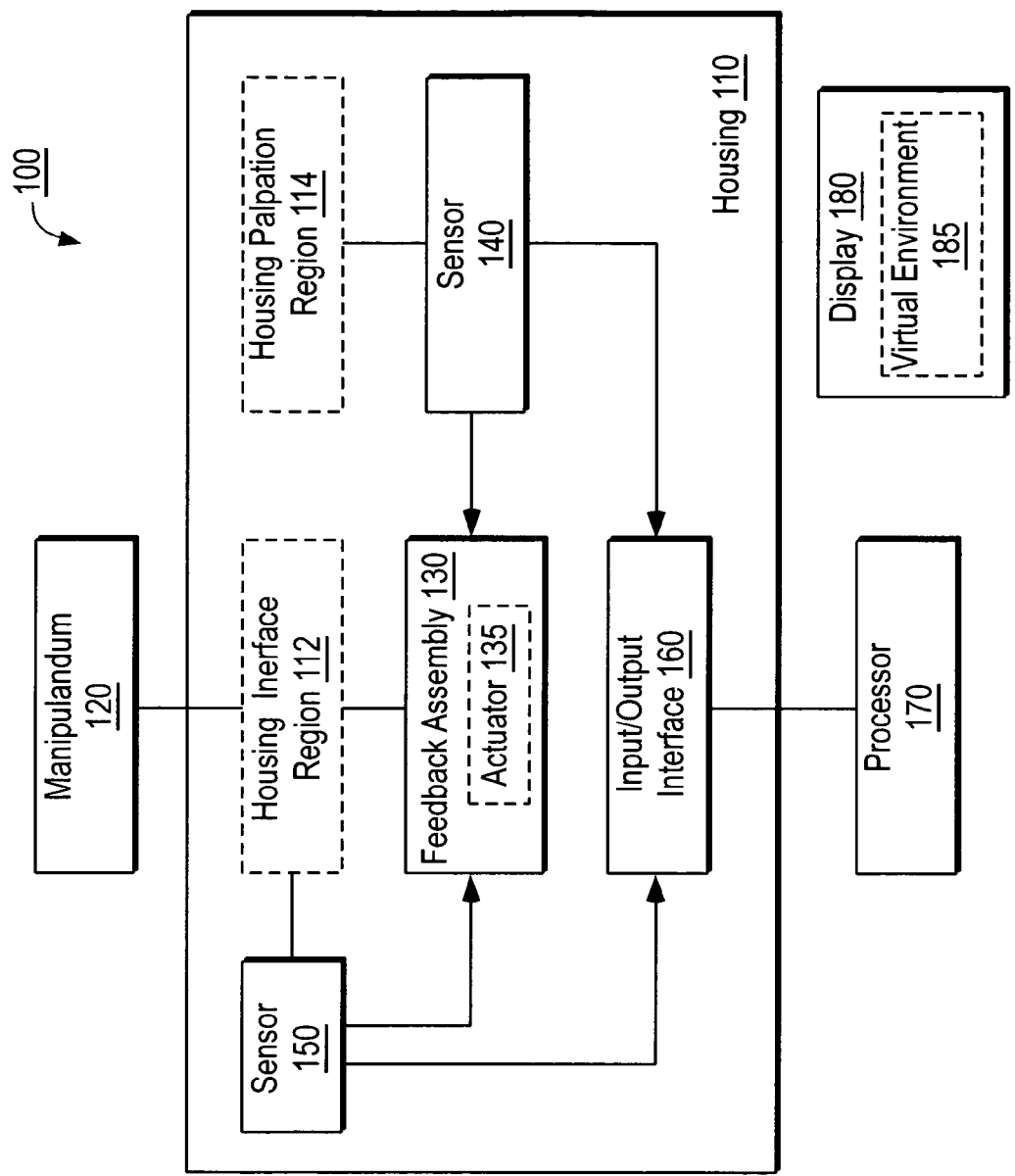
FIG. 1 shows a system block diagram of a simulation system having a palpation region, according to an embodiment of the invention.

FIG. 1 shows a system block diagram of a simulation system having a palpation region, according to an embodiment of the invention. As shown in FIG. 1, simulation system 100 includes housing 110, manipulandum 120, feedback assembly 130, sensors 140 and 150, input/output interface 160, processor 170 and display 180. Housing 110 includes housing interface region 112 and housing palpation region 114. Feedback assembly 130 includes an actuator 135. Display 180 includes virtual environment 185. In this embodiment, feedback assembly 130, sensors 140 and 150, and input/output interface 160 are disposed within housing 110.

Figure 2:
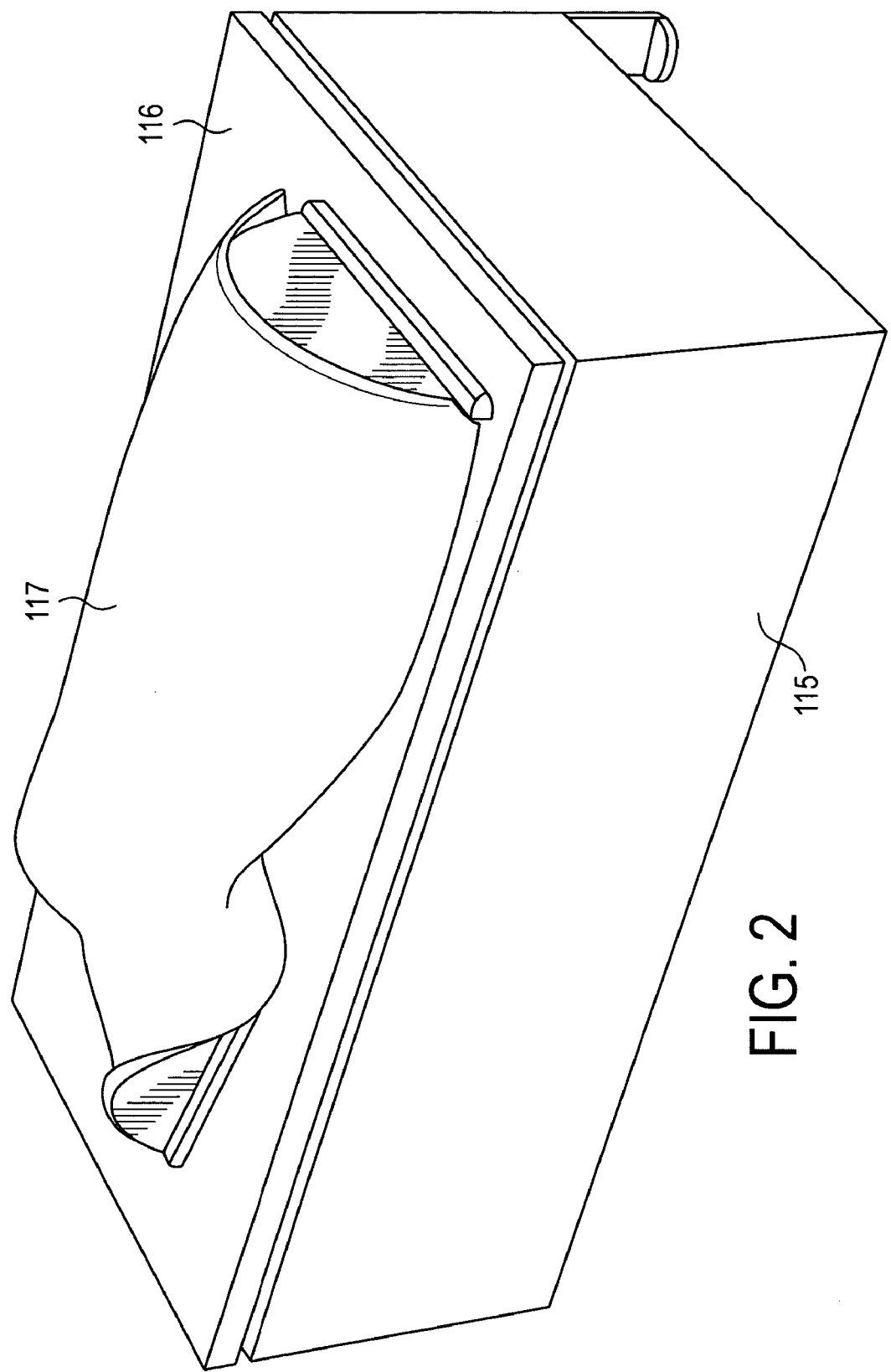
FIG. 2 shows a perspective view of a housing configured to simulate a patient's leg, according to an embodiment of the invention.
Figure 3:
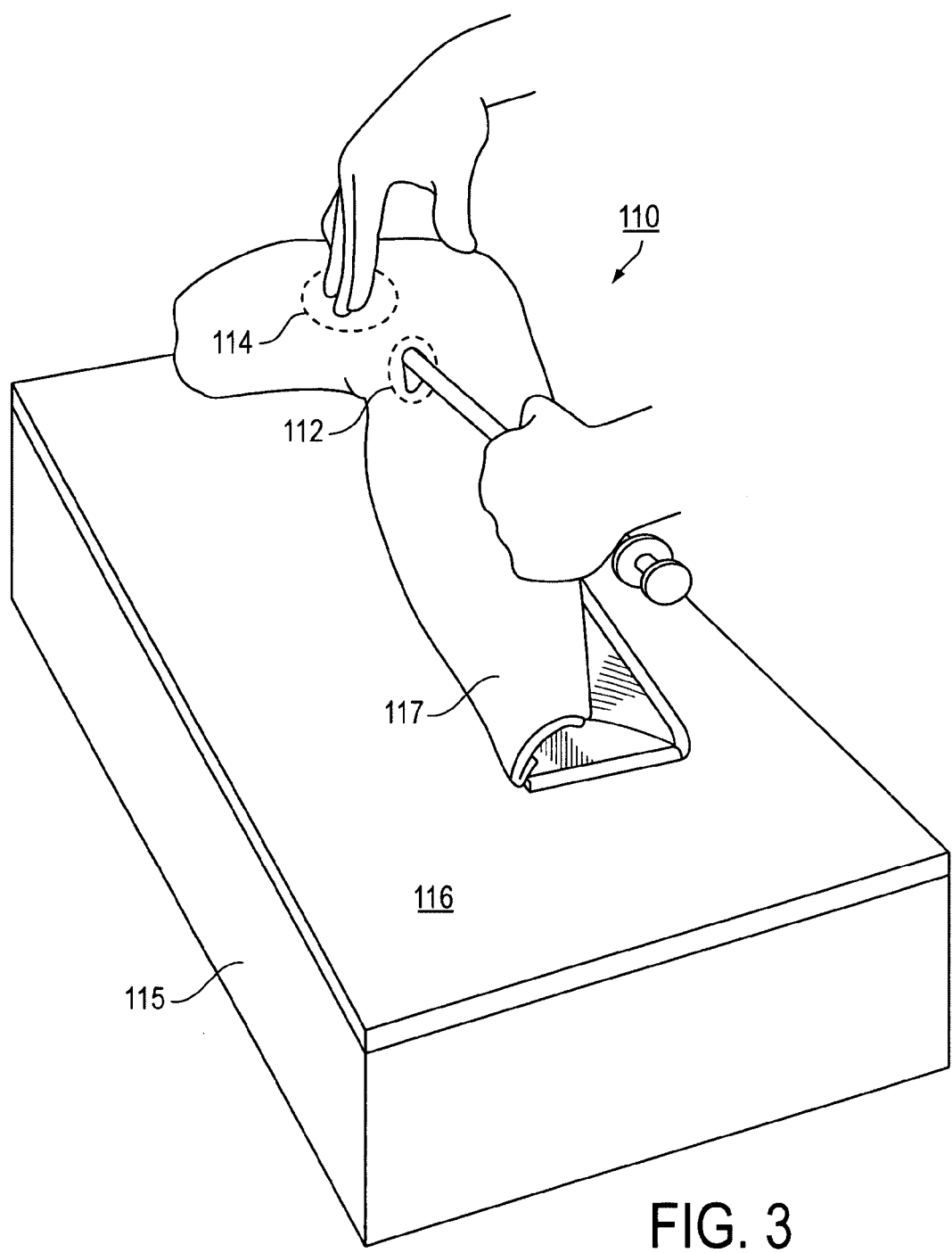
FIG. 3 shows a perspective view of the housing shown FIG. 2 during a simulation of a medical procedure.

Housing 110 can be any type of structure that defines a palpation region 114. Housing 110 can also be configured such that several components of the simulation system 110 are disposed within housing 110. Such components can include, for example, feedback assembly 130, sensors 140 and 150, and input/output interface 160. In alternative embodiments, the actuator, sensors, and/or input/output interface can be disposed outside of the housing 110. FIGS. 2 and 3 show an example of housing 110.

More specifically, FIG. 2 shows a perspective view of a housing configured to simulate a patient's leg, according to an embodiment of the invention. FIG. 3 shows a perspective view of the housing shown in FIG. 2 during a simulation of a medical procedure. As shown in FIG. 2, housing 110 includes a base portion 115, a top portion 116, and an anatomical structure 117 disposed on the top portion 116. In this embodiment, the anatomical structure 117 simulates a patient's left leg and includes an outer membrane that simulates tissue such as skin. In other embodiments, the anatomical structure can simulate other body portions of a simulated patient, such as for example, a right leg, an arm, a torso, etc. The anatomical structure 117 can include an internal frame having solid portions that support the outer membrane and open portions through which the user can move the manipulandum 120 and palpate the simulated leg. The outer membrane of the anatomical structure 117, for example, can be made of a flexible material such as rubber or fabric-covered rubber. Similarly, the internal frame of the anatomical structure 117, for example, can be made of a rigid, semi-rigid or flexible plastic or rubber. As shown in FIG. 3, housing 110 includes interface region 112 and palpation region 114 each of which includes a different portion of the surface of anatomical structure 117.

Housing interface region 112 is a portion of housing 110 where the manipulandum 120 can interact with housing 110. In this embodiment, the manipulandum 120 penetrates the outer surface of anatomical structure 117 at interface region 112. In the virtual environment 185, the medical device simulated by manipulandum 120 enters the simulated patient's leg at a simulated anatomical region corresponding to housing interface region 112.

Housing palpation region 114 is a portion of housing 110 where a user (e.g., a medical practitioner) can palpate the simulated patient body portion. Such palpation can be any type of touching of the simulated body portion without an intervening medical device. Such palpation can include, for example, applying pressure, feeling for a rebound response based on applied pressure, or receiving a spontaneous response from the patient (e.g., reading a pulse). For example, as shown in FIG. 3, the user can palpate a simulated patient leg during the simulation of an MIVH procedure. In this simulated procedure, the user palpates the simulated patient leg in the sense that the user applies pressure to the palpation region 114 to simulate the process of relocating the saphenous vein and surrounding fat tissue within the simulated patient's leg tissue while manipulandum 120, in the form of a simulated dissector device, is being moved through the patient's leg by the user's other hand. In other words, the user moves manipulandum 120 to simulate the production of a tunnel within the fat tissue and adjacent to the saphenous vein.

Returning to FIG. 1, manipulandum 120 can be any type of interface device that a user can manipulate to interact with the simulation system 100. For example, manipulandum 120 can be a device that physically resembles a medical device. In such an embodiment where manipulandum 120 simulates or replicates a medical device, the manipulandum is referred to herein as a simulated medical device. In alternative embodiments, manipulandum 120 can be an actual medical device; in such embodiments, the simulation system 100 is configured to operate in conjunction with the actual medical device.

In some embodiments, the manipulandum 120 can have one portion external to the housing 110 and another portion internal to the housing 110. In such embodiments, for example, the two portions of the manipulandum can be monolithically formed, integrally formed or removably coupled, as appropriate for a given simulation. In other embodiments, the manipulandum has an external portion only, while the effect or feel of an internal portion of the manipulandum is simulated by the simulation system.

In one embodiment where the manipulandum has two portions, the manipulandum has multiple configurations, each corresponding to a different external portion of the manipulandum that can be removably coupled to the internal portion of manipulandum. In an embodiment where the manipulandum has two configurations, for example, the external portion of the manipulandum can be a simulated dissector endoscope while the manipulandum is in a first configuration; the external portion of the manipulandum can be a simulated electrocautery endoscope while the manipulandum is in a second configuration. In this embodiment, the two external portions of the manipulandum can be used to simulate an MIVH procedure for harvesting a saphenous vein from a leg. These two portions of the manipulandum can simulate, for example, the dissector endoscope and the electrocautery endoscope described in U.S. patent application Publication 2003/0130674, entitled "Treatment Sheath for Endoscopic Blood Vessel Harvesting;" the entirety of the disclosure is incorporated herein by reference.

Feedback assembly 130 is any type of assembly or device that can output haptic feedback to manipulandum 120. Feedback assembly 130 includes an actuator 135 that receives a signal and outputs a force based on the signal. As described below, the signal received by actuator 135 can be provided, for example, by processor 170 and in conjunction with the virtual environment displayed on display 180. Feedback assembly 130 can be configured such that the force output by actuator 135 is translated, for example, to manipulandum 120. For example, feedback assembly 130 can be configured such that the force output by the actuator 135 is translated to an internal end portion of manipulandum 120. Feedback assembly 130 can be configured to provide, for example, haptic feedback to the manipulandum 120 in three degrees-of-freedom and to allow the manipulandum to have a range of motion in, for example, six degrees-of-freedom.

Figure 4:
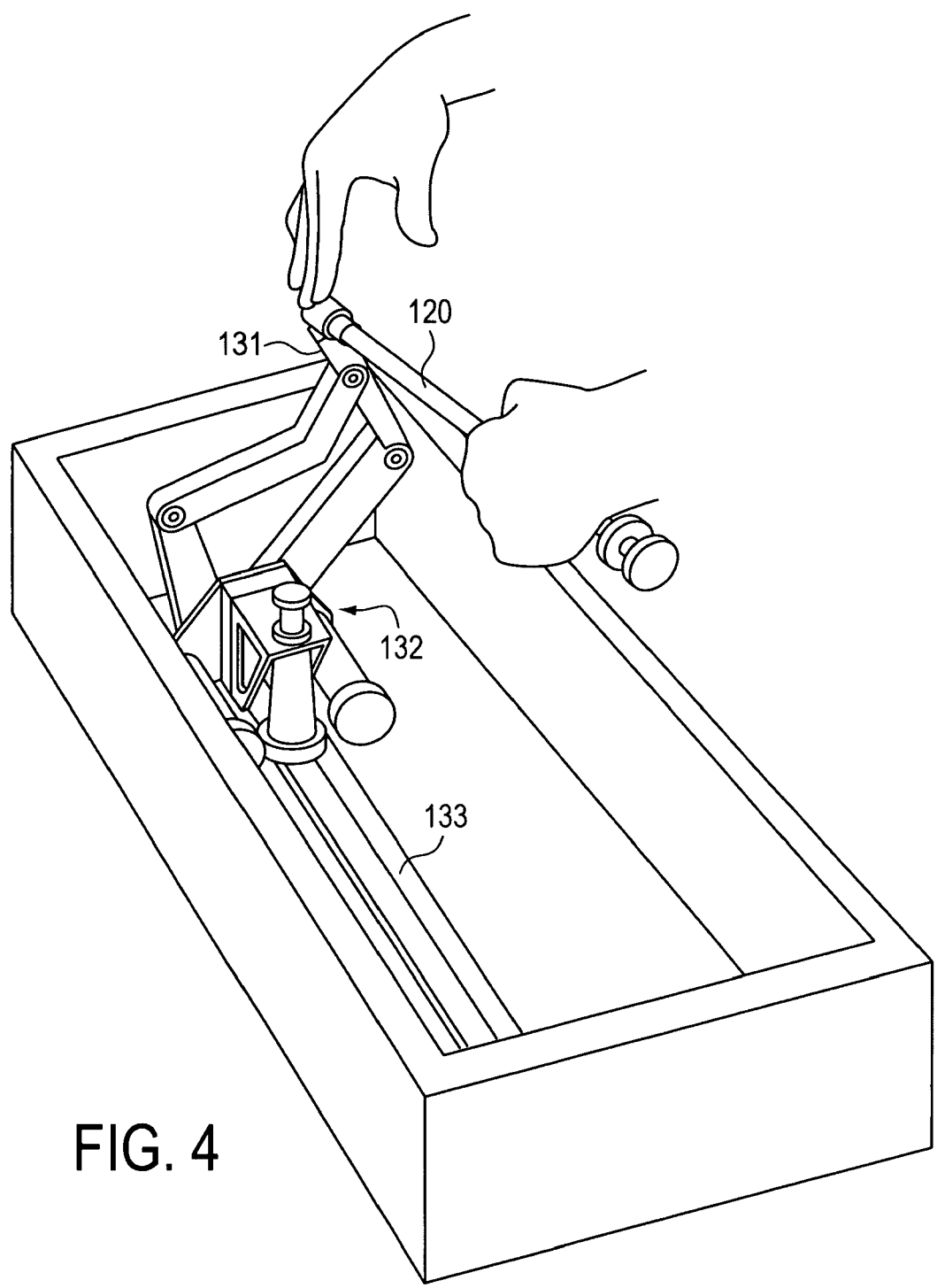
FIGS. 4 and 5 each show a perspective view of a feedback assembly within housing, according to an embodiment of the invention.
Figure 5:
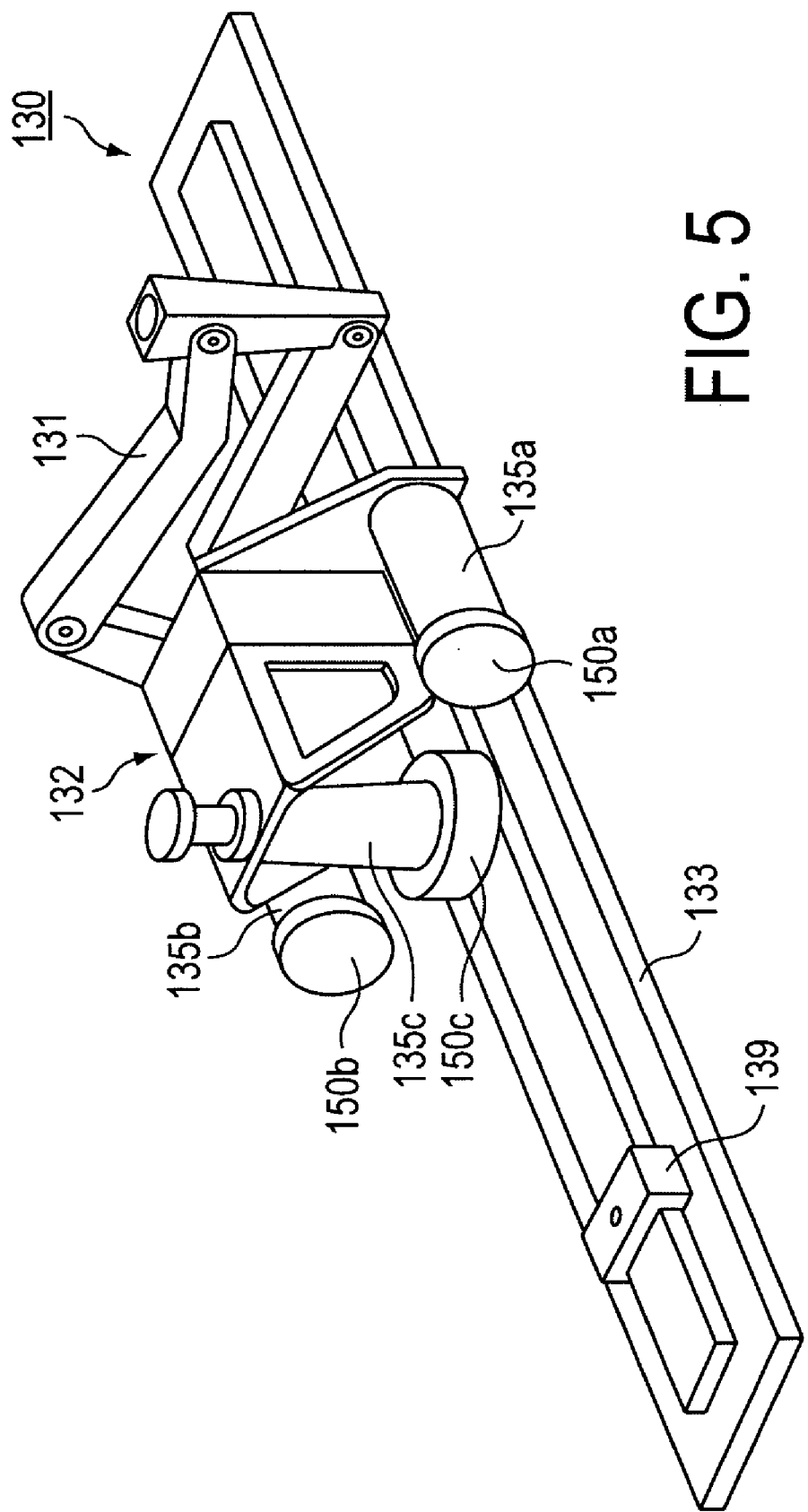

FIGS. 4 and 5 show perspective views of a feedback assembly 130, according to an embodiment of the invention. As shown in FIG. 4, feedback assembly 130 can be disposed within housing 110. Feedback assembly 130 includes, for example, a five-bar linkage 131 on a carriage 132 mounted on a linear bearing 133. An example of such a five-bar linkage is described in U.S. Pat. No. 5,828,197, entitled "Mechanical Interface Having Multiple Grounded Actuators," the disclosure of which is incorporated herein by reference. Such a feedback assembly 130 can provide haptic feedback, for example, in three degrees-of-freedom to an internal portion of the manipulandum 130.

Sensors 140 and 150 can be any type of appropriate sensors that detect position and/or orientation of manipulandum 120 and housing palpation region 114, respectively. Sensor 150 can be, for example, a sensor that measures the movement of manipulandum 120 in six degrees-of-freedom (e.g., x, y, z, pitch, yaw and roll). Sensor 150 can be disposed within feedback assembly 130 such that a change in the position and/or orientation of manipulandum 120 is translated through feedback assembly 130 and detected by sensor 10. Alternatively, sensor 150 can be disposed at an interior end portion of manipulandum 120. Sensor 150 can be a single sensor or a combination of multiple sensors. In some embodiments, sensor 150 can be configured to measure the position and/or orientation of manipulandum 120 with respect to an absolute coordinate system. In other embodiments, sensor 150 can be configured to measure the position and/or orientation of manipulandum 120 with respect to a relative coordinate system.

FIG. 5 shows an example of an embodiment of a feedback assembly 130 having three sensors and three actuators. In this embodiments, the three sensors are optical encoders 150*a*, 150*b* and 150*c*; the three actuators are motors 135*a*, 135*b* and 135*c*. Motors 135*a* and 135*b* each use a capstan to drive a cable (not shown in FIG. 5) attached to one of the two arcuate members of the five-bar link 131, providing for two degrees of freedom. Optical encoders 150*a* and 150*b* detect motion of motors 135*a* and 135*b*, and thus the position of the five-bar link 131 in these two degrees of freedom. Motor 135*c* uses a capstan to drive against a cable (not shown) grounded to the case and parallel to linear bearing 139. Motion of motor 135*c* is sensed via optical encoder 150*c*, and thus motion of the movable carriage 132 with respect to the fixed cable can be obtained, providing the third degree of freedom. Three more degrees of freedom of manipulandum 120 can be measured, namely pitch, yaw and rotation about the long axis. Optical encoders (not shown), such as the HP rose encoder, can be embedded in a pitch/yaw/roll joint attached to the tip of the five-bar link 131 to measure these three additional degrees of freedom.

When based on a relative coordinate system, sensor 150 can be calibrated through the use of a "home position" to which manipulandum 120 returns, for example, upon power up of the simulation system 100. Upon such power up, a zero position value and starting orientation values can be assigned to sensor 150 based on the position and orientation of manipulandum 120 in its home position. Further details for calibrating a sensor 150 based on a relative coordinate system are discussed in U.S. Pat. No. 6,697,748, the disclosure of which is incorporated herein by reference.

Figure 6:
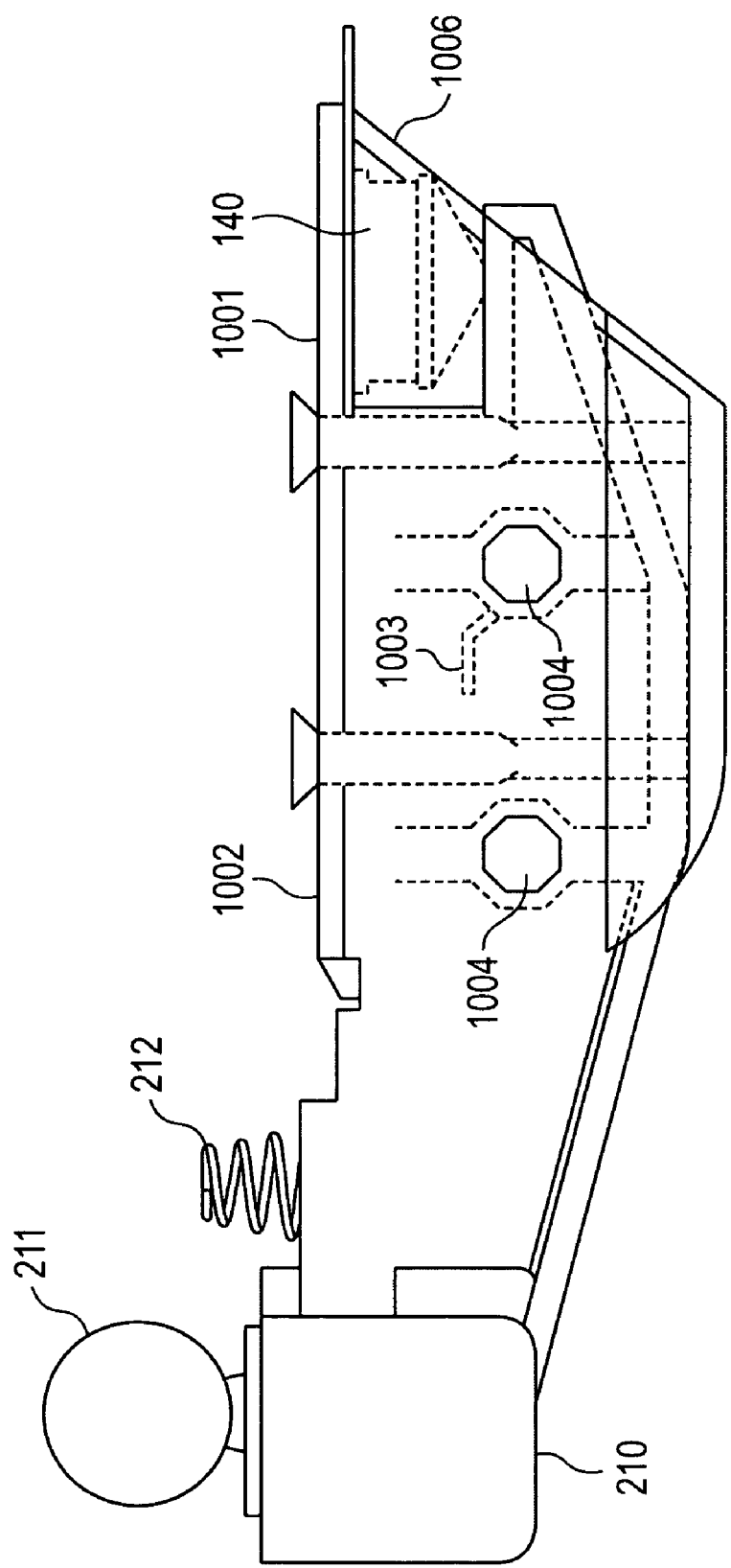
FIG. 6 shows a perspective view of a sensor mounted within a housing assembly, according to an embodiment of the invention.
Figure 7:
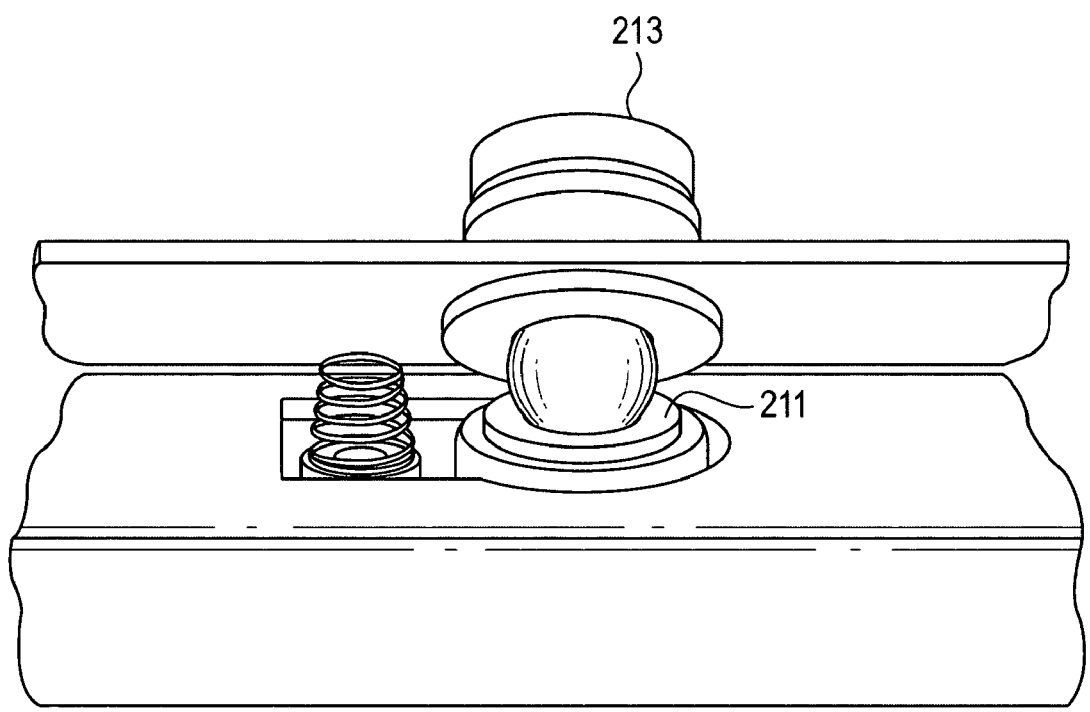
FIG. 7 shows a perspective view of a sensor disposed within housing, according to an embodiment of the invention.

Sensor 140 can be, for example, a polymer-thick-film (PTF) force sensor, which exhibits a decrease in resistance with an increase in force, such as those provided by Interlink Electronics of Carmarillo, Calif. Sensor 140 can be a single sensor or a combination of multiple sensors. In some embodiments, sensor 140 can be disposed at an interior end portion of manipulandum 120. In other embodiments, sensor 140 can be disposed within housing 110. For example, for the embodiment shown in FIGS. 2 through 5, four sensors 140 are disposed between the housing base portion 115 and the housing top portion 116. More specifically, each sensor 140 from the set of four sensors 140 is located near a respective corner of the housing 110 between the housing base portion 115 and the housing top portion 116. FIG. 6 shows a perspective view of a sensor 140 mounted within a housing assembly 210, according to an embodiment of the invention. FIG. 7 shows a perspective view of a sensor 140 disposed within housing 110, according to an embodiment of the invention.

As shown in FIGS. 6 and 7, housing assembly 210 includes a male fastener portion 211, an electrical spring connector, 212, an electrical case contact wire 1002, a pivot pin 1003, a frame 1001 with three locating holes, a sensor 140, a resilient member 1006, and a pivot member 1007, also with three locating holes spaced similarly to the holes in frame 1001. Male fastener portion 211 is fitted into an appropriate socket in pivot member 1007. Pivot pin 1003 is inserted through one of three sets of aligned holes in frame 1001 and pivot member 1007. Forces on male fastener portion 211 cause pivot member 1007 to pivot around pivot pin 1003, causing the end of pivot member 1007 to compress resilient member 1006 against sensor 140. Sensor 140 measures the force applied to male fastener portion 211. Sensor 140 can be, for example, a PTF force sensor provided by Interlink Electronics of Carmarillo, Calif. Moving the pivot pin 1003 to a different hole can provide a different mechanical advantage in the simple lever system, thus providing adjustable mechanical amplification of the force on male fastener portion 211. Electrical spring connector 212 can provide a grounding path for electrostatic discharge.

A housing assembly 210 is disposed within each corner portion of the housing base portion 115 such that the respective male fastener portion 211 and electrical spring connector 212 protrude from that corner portion of the housing base portion 115. The protruding male fastener portion 211 and electrical spring connector 212 at each corner portion of housing base portion 115 contacts a respective corner portion of housing top portion 116. In other words, as best shown in FIG. 7, male fastener portion 211 disposed within the housing base portion 115 mates with a respective female fastener portion 213 disposed within the housing top portion 116. The male fastener portion 211 and female fastener portion 213 can be, for example, a Tree-Lok Fastener provided by ITW Fastex of Des Plaines, Ill.

When the four male fastener portions 211 mate with the four respective female fastener portions 213 (i.e., when the housing top portion 116 is disposed on the housing bottom portion 115), the magnitude and position of a force applied to the palpation region 114 of housing 110 can be determined based on measurements performed by the four sensors 150. The process of determining the magnitude and position of forces applied to the palpation region 114 of housing 110 is further described by reference to FIG. 8.

Figure 8:
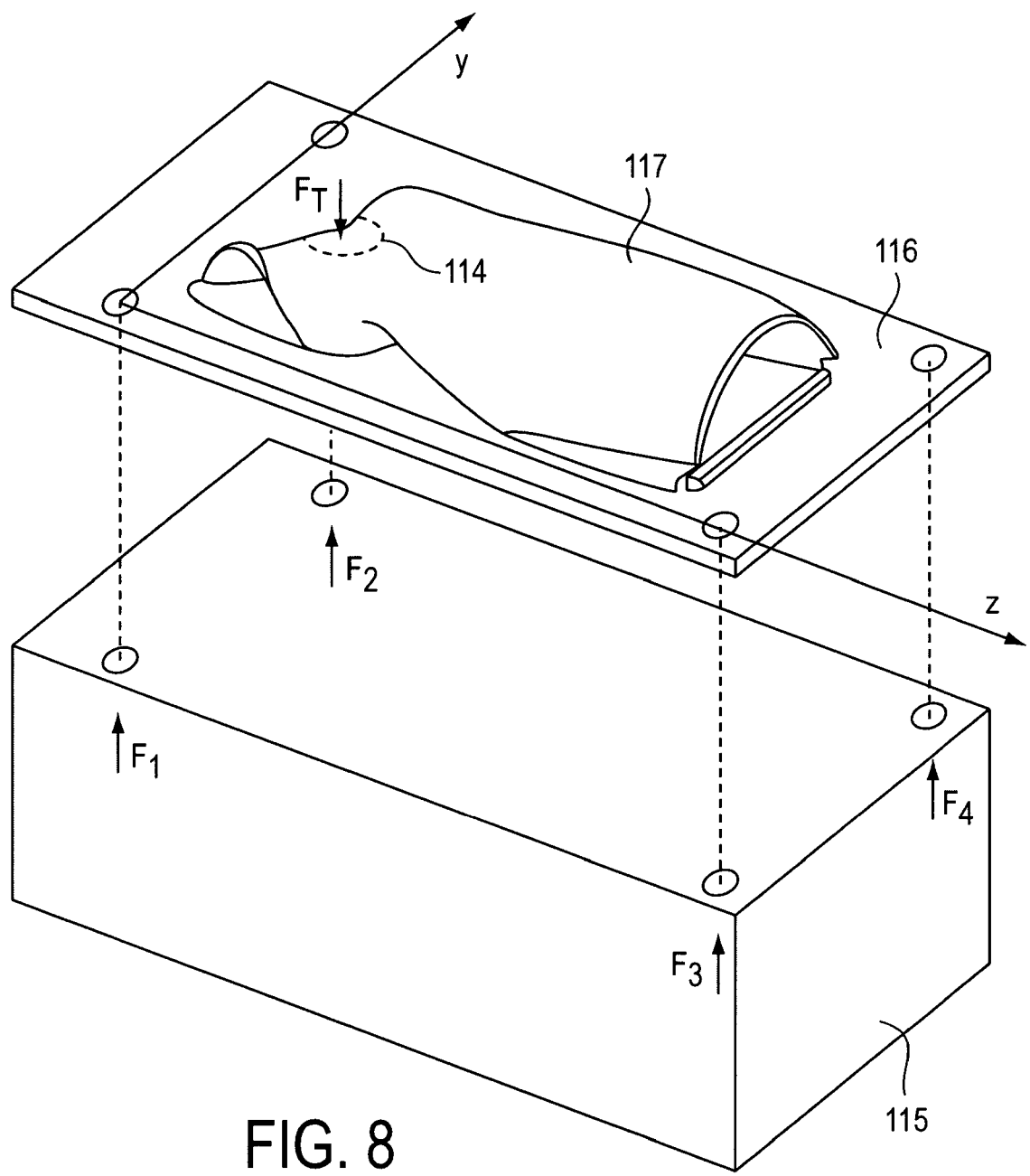
FIG. 8 shows an assembly view of the housing shown in FIGS. 2-7.

FIG. 8 shows an assembly view of the housing shown in FIGS. 2-7. As shown in FIG. 8, the four sensors are disposed within the housing bottom portion 115 so as to measure the upward forces that support the housing top portion 116. When the user is not applying palpation force to the housing top portion 116, the output of sensors 150 is sampled and these outputs are taken as the baseline condition (i.e., no palpation or zero force) for each of the sensors. When an actual palpation force, $F_T$, (i.e., the force applied by a user of the simulation system to the palpation region 114) is present, the output of sensors 156 will reflect the larger-magnitude forces necessary to support the top in this condition. Calibration of the sensor output by standard techniques, using the zero force condition and a scaling factor determined by application of test forces to the four sensors, allows the sensor outputs to be converted to a measure of the forces over and above the gravitational baseline present at each sensor 150. These additional forces are due to the palpation force applied by the user, and can be understood, from the conditions for static equilibrium, to collectively sum to a value equal and opposite the total applied palpation force. Further, static equilibrium provides that the forces oppose rotation about any axis. These conditions of static equilibrium can then be used to solve for the total palpation force. Forces $F_1$, $F_2$, $F_3$ and $F_4$, correspond to the forces at each of the four corner portions of the housing 110 at which a respective sensor 150 is located. Based on the magnitude of these four forces, $F_1$, $F_2$, $F_3$ and $F_4$, the position and magnitude of the total palpation force, $F_T$, can be determined from the conditions of static equilibrium as noted above. Assuming a two-dimensional coordinate system (x, y) as shown in FIG. 8, each force sensor 150 has a respective location $(x_1, y_1)$, $(x_2, y_2)$, $(x_3, y_3)$ and $(x_4, y_4)$. The force sensors 150 each oppose a portion of the force, $F_T$, and these are represented as the four forces, $F_1$, $F_2$, $F_3$ and $F_4$. From these forces, the magnitude and location $(x_t, y_t)$ of the total palpation force, $F_T$, can be determined from the following three equations that represent a zero net moment around the x and y axes, and a zero net force, respectively:

$$\sum_{i=1}^{4} F_i \cdot x_i = F_t \cdot x_t;$$

$$\sum_{i=1}^{4} F_i \cdot y_i = F_t \cdot y_t;$$

$$F_t = \sum_{i=1}^{4} F_i.$$

With the magnitude of $F_T$ determined here, this value can be substituted into the first two equations to determine the position of the applied palpation force as follows:

$$x_t = \frac{\sum_{i=1}^{4} F_i \cdot x_i}{F_t}; \text{ and } y_t = \frac{\sum_{i=1}^{4} F_i \cdot y_i}{F_t}.$$

These equations can be implemented in software operating, for example, on processor 170. Such software can also perform additional functions, such as for example, signal conditioning, noise filtering, the elimination of the baseline signal associated with gravity, scaling and linearity correction as appropriate for a given type of sensor 150. In addition, such software can also perform other signal processing, such as threshold comparison, minima and maxima detection, use of an embedded processor, etc. such as that disclosed in U.S. Pat. No. 4,511,760, entitled "Force Sensing Data Input Device Responding to the Release of Pressure Force," the disclosure of which is incorporated herein by reference. Such additional functions are typically performed before the calculation of the above equations to determine the magnitude and/or location of the palpation force, $F_T$. The resultant force vector can be used in the software associated with the virtual environment to deform the tissue in the virtual environment in response to user palpation. The deformation can be a simple geometric deformation, whereby motion of the tissues is a simple function of the force and position of the total palpation, and diminishes with distance from the palpation position. Alternately, a more complex physical model, such as a finite element model of the properties of the different tissues, can be used to deform the tissue in the virtual environment in response to the palpation force applied by the user. The resultant deformation can then be displayed on display 180 in the endoscopic view, or other views of virtual environment 185; this enables the user to practice and gain proficiency in techniques of palpating the leg in coordination with manipulation of the medical instrument to most effectively separate and harvest the vein from the surrounding tissue.

In alternative embodiments, the sensor configured to measure forces applied to the housing palpation region is disposed within the housing palpation region itself. For example, such a sensor can be a pressure-sensitive sensor disposed with a housing palpation region having a rigid construction; in such an arrangement, the sensor can measure the z-direction (orthogonal to the x and y axes) component of applied forces. In other embodiments, the sensor can be one or more strain gauges configured to measures three-dimensional components of applied forces.

Returning to FIG. 1, processor 170 can be, for example, a commercially available microprocessor. Alternatively, the processor 170 can be an application-specific integrated circuit (ASIC) or a combination of ASICs, which are designed to achieve one or more specific functions, or enable one or more specific devices or applications. In yet another embodiment, the processor 170 can be an analog or digital circuit, or a combination of multiple circuits.

Processor 170 includes a memory component (not shown in FIG. 1). The memory component can include one or more types of memory. For example, the memory component can include a read only memory (ROM) component and a random access memory (RAM) component. The memory component can also include other types of memory that are suitable for storing data or software in a form retrievable by the processor 170. For example, electronically programmable read only memory (EPROM), erasable electronically programmable read only memory (EEPROM), flash memory, as well as other suitable forms of memory can be included within the memory component. The processor 170 can also include a variety of other components, such as for example, co-processors, graphics processors, etc., depending upon the desired functionality of the device.

The simulation system 100 is configured such that a user (e.g., a medical practitioner) moves manipulandum 120 and palpates the palpation region 114 in conjunction with viewing the virtual environment 185 on display 180. In other words, a user receives haptic output at the manipulandum 120 and/or palpation region 114 while also viewing the virtual environment 185, which is provided in coordination with the haptic output. FIGS. 9 through 13 show examples of a virtual environment for an MIVH procedure, according to an embodiment of the invention.

Figure 9:
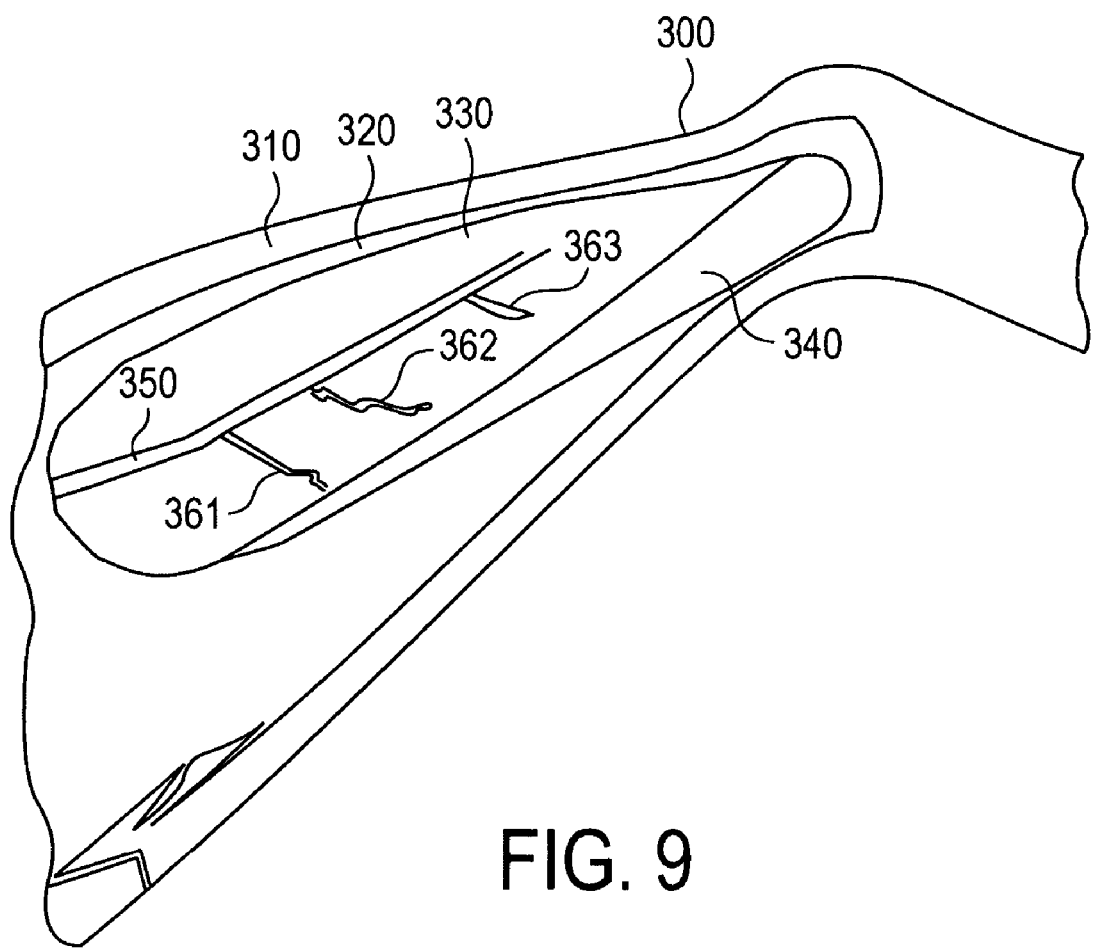
FIG. 9 shows the cross-sectional display of a leg model within a virtual environment for a minimally invasive vein harvesting (MIVH) procedure, according to an embodiment of the invention.

FIG. 9 shows the cross-sectional display of a leg model within a virtual environment for an MIVH procedure, according to an embodiment of the invention. As shown in FIG. 9, the leg model includes several different types of tissue as well as the saphenous vein and its smaller branch veins. More specifically, the leg model shown in FIG. 9 includes tissue layers 310 through 340: tissue layer 310 represents the skin and outer most muscle layer; tissue layer 320 represents an inner muscle layer; tissue layer 330 represents a fat layer within which the saphenous vein 350 is disposed; and tissue layer 340 represents a bone within the virtual leg. Saphenous vein 350 is connected to several smaller branch veins including veins 361, 362 and 363.

The various tissue layers 310 through 340 of the virtual leg model can affect the manner in which haptic feedback is provided by feedback assembly 130. For example, feedback assembly 130 can provide haptic feedback to manipulandum 120 as a function of the position and/or orientation of the end portion of the manipulandum 120 relative to the various tissue layers 310 through 340 of the virtual leg model. In other words, the user moving manipulandum 120 can feel different levels of resistance relating to the position and/or orientation of the end portion of the manipulandum 120 relative to a given tissue level 310 through 340 of the virtual leg model.

Figure 10:
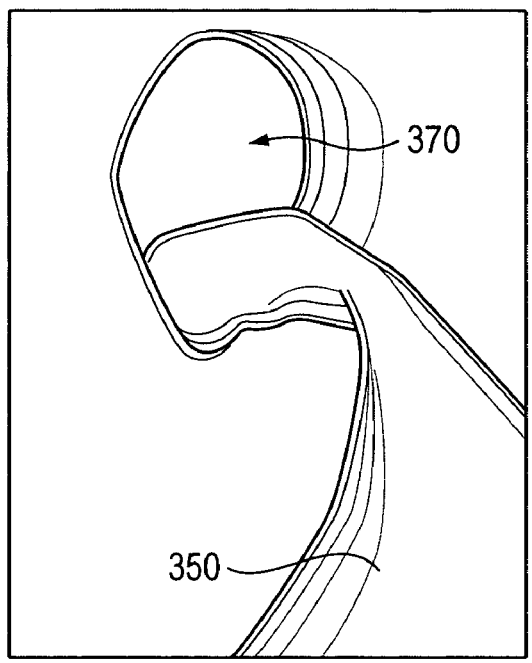
FIG. 10 shows an example of a display of the virtual environment during a portion of an MIVH procedure where a dissector device separates the vein from surrounding tissue, according to an embodiment of the invention.

FIG. 10 shows an example of a display of the virtual environment during a portion of an MIVH procedure where a dissector device separates the saphenous vein from surrounding tissue, according to an embodiment of the invention. For this portion of the simulation of the MIVH procedure, manipulandum 120 is in a configuration that simulates an endoscopic dissector device having a rigid shaft (not shown) and a camera (not shown) disposed within a transparent conical tip. In an actual MIVH procedure, the medical practitioner can watch a video display showing the interior of the leg via the camera within the dissector device.

Simulation system 100 replicates this arrangement by providing a virtual environment 185 on display 180 based on the user's movement of manipulandum 120 and the user's palpation of palpation region 114 of housing 110. In other words, as the user moves manipulandum 120 and palpates palpation region 114 of housing 110, the virtual environment 185 on display 180 approximates the view that would be produced by the movement of the dissector device and by the palpation of the leg in an actual MIVH procedure.

Figure 15:
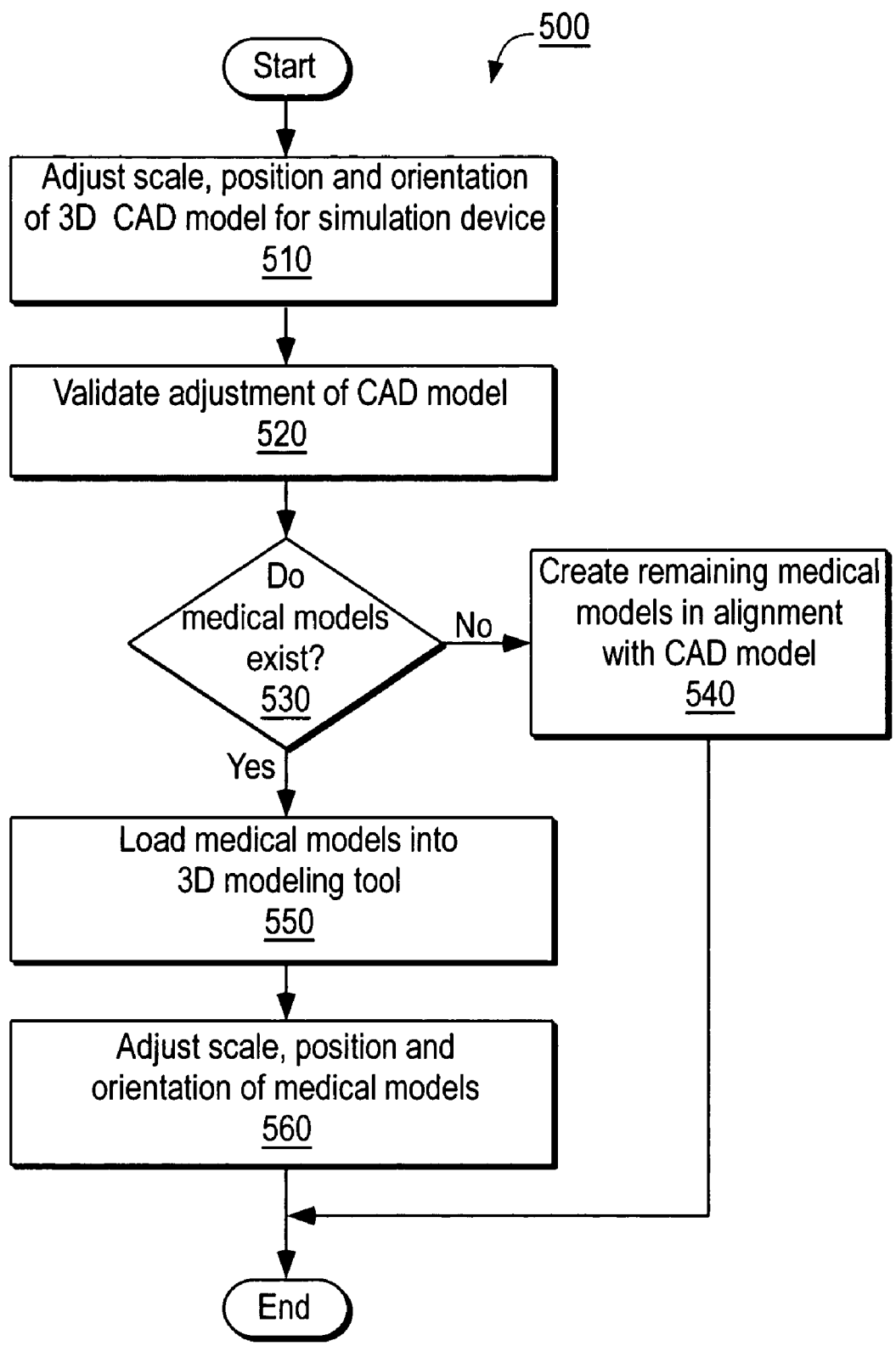
FIG. 15 is a flow chart for the registration process between the simulation space and the virtual space, according to an embodiment of the invention.

Because the user moves manipulandum 120 and palpates the palpation region 114 in coordination with viewing the virtual environment 185 on display 180, a registration process is appropriate. This registration process can be performed once for each distinct set of anatomical structures 117 that will be used with the simulator system 100. Each distinct set of anatomical structures 117 represents, for example, the anatomy of a unique patient or case. FIG. 15 is a flow chart for the registration process 500 between simulation space and the virtual space, according to an embodiment of the invention.

As shown in FIG. 15, at step 510, a three-dimensional computer-aided design (CAD) model of the simulator device (e.g., housing 110 and surface of anatomical structure 117) is adjusted to match the scale, position, and orientation of the virtual environment's workspace as reported by the sensors used during the simulation. For example, in an embodiment for a MIVH procedure, the scale is millimeters, the orientation corresponds to the length of the housing 110 along the x-axis, and the origin position is at the insertion point for manipulandum 120 into housing interface region 114. The CAD model of the surface 370 of the leg is shown in FIG. 9. At step 520, the accuracy of this adjustment can be validated. The accuracy of this adjustment can be validated, for example, by selecting three distinct fiducial registration points on housing 110, such fiducial points being molded into housing 110, and verifying that when the tip of manipulandum 120 contacts the physical points within housing 110, the tip of the virtual device (e.g., endoscopic dissector device) contacts the corresponding positions on the CAD model. This CAD model alignment can be performed once for a given anatomical structure 117 for the simulation system 100.

Once the CAD model is exported and oriented into the space of the virtual environment and validated (steps 510 and 520), each medical model associated with an anatomical structure and to be used as the basis for a simulation can be registered to the CAD model. At conditional step 530, a determination is made as to whether all of the appropriate medical models exist. If the medical models have not yet been created, at step 540 the medical modeler can create them in alignment with the oriented CAD model. If the medical models already exist, then they can be loaded into a 3D modeling tool at step 550 and registered to the CAD model at step 560. This may involve, for example, scaling, translating, and rotating the anatomical model. In addition, the shape of the model can be tailored to better match the shape of the housing 110 and manipulandum 120. For example, the palpation region of the CAD model can be aligned tangent to the same anatomical region on the leg model within the virtual environment. In this way, when the user's hand touches the surface of the anatomical structure 117 from the outside of housing 110, or when the end portion of manipulandum 120 touches the surface of the anatomical structure 117 from the inside of the housing 110, the software provide a display of a collision with the skin of the leg within the virtual environment 185.

Now that the position and orientation of the anatomical model within the virtual environment is aligned with the physical model of the simulation system 100, the software can be executed with the expectation that the physical and virtual models will be synchronized. When the user moves manipulandum 120 with respect to housing interface portion 112 and palpates region 114, the movements can be accurately reflected in the virtual environment 185. For example, as the user palpates palpation region 114, the palpation will result in a corresponding movement or deformation of the virtual tissue layers 310 through 340 at the same position and magnitude in the virtual environment as in the physical environment. This allows the simulation user to maintain the sense that their physical manipulations are accurately reflected in the virtual environment.

In this portion of the simulation involving the dissector device, a tunnel 370 adjacent to or surrounding the saphenous vein 350 is created within virtual environment 185 as a user moves manipulandum 120 and palpates palpation region 114 of housing 110. While this tunnel 370 is being produced by the user's movements, the user can also receive haptic feedback at manipulandum 120 and/or palpation region 114 of housing 110 in coordination with the display of virtual environment 185.

Figure 11:
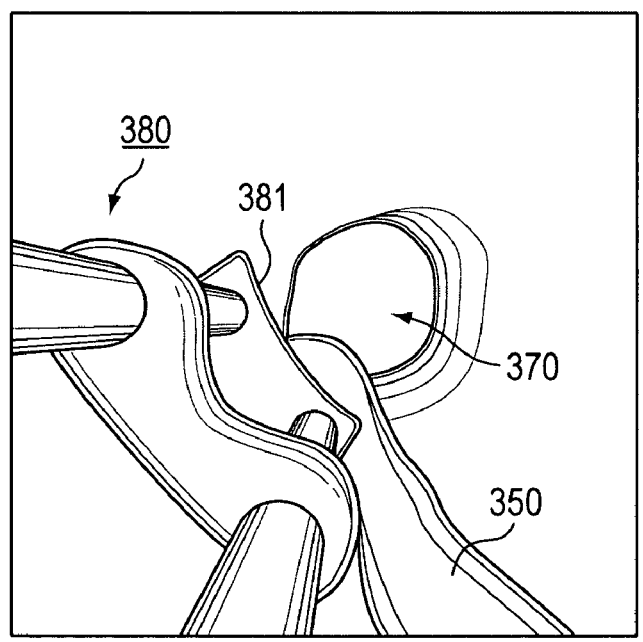
FIG. 11 shows an example of the virtual environment where the electrocautery device is inserted into tunnel, according to an embodiment of the invention.
Figure 12:
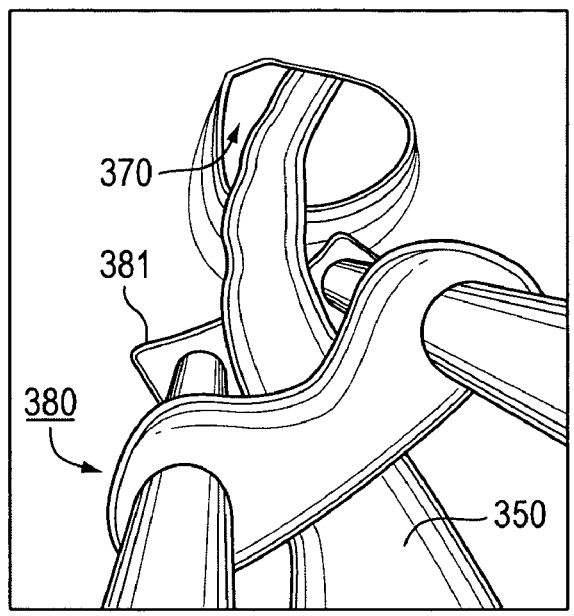
FIG. 12 shows an example of the virtual environment where the electrocautery device captures the saphenous vein, according to an embodiment of the invention.
Figure 13:
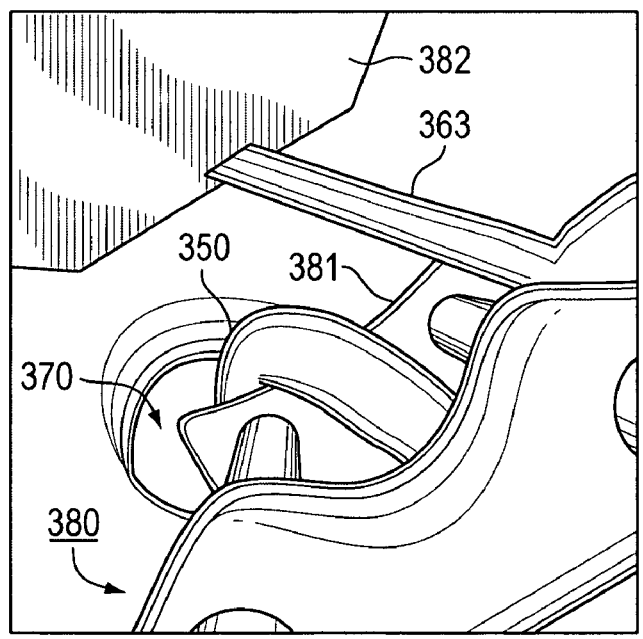
FIG. 13 shows an example of the virtual environment where the electrocautery device cauterizes a branch vein of the saphenous vein, according to an embodiment of the invention.

FIGS. 11 through 13 show an example of a display of the virtual environment, representing the endoscopic view through a camera within an electrocautery deviceduring a portion of an MIVH procedure, according to an embodiment of the invention. For this portion of the simulation of the MIVH procedure, manipulandum 120 is in a configuration that simulates an endoscopic electrocautery device 380 having a rigid shaft, a camera (not shown), a capture portion 381 and an extendible cauterizing portion 382. More specifically, FIG. 11 shows an example of the virtual environment where the electrocautery device 380 is inserted into tunnel 370, according to an embodiment of the invention. FIG. 12 shows an example of the virtual environment where the electrocautery device 380 captures the saphenous vein 350, according to an embodiment of the invention. FIG. 13 shows an example of the virtual environment where the extendible cauterizing portion 382 of the electrocautery device 380 is activated by a footpedal (not shown) to cauterize a branch vein 363 of the saphenous vein 350, according to an embodiment of the invention.

The software for producing the display of the virtual environment 185 can be executed by processor 170. Although FIGS. 11 through 13 relate to a virtual environment associated with a MIVH procedure, in other embodiments, the software can produce the display of virtual environments associated with another procedures as appropriate. The software can, for example, be based on a technique for displaying three-dimensional surface images through the use of a number of textured surface models embedded in a volume. The surface models can represent deformable as well as non-deformable substances such as skin, veins, arteries, nerves, muscles, and bones. A given volume can be pre-tessellated into cubes. The cubes can be used both to simulate the physics of the volume and to serve as a medium to apply, for example, the "Marching Cubes" algorithm to generate polygonal surfaces. The location of the polygonal surface can be determined by an implicit surface function applied at the tool tip, i.e., where the cutting occurs. The "Marching Cubes" and similar algorithms use a case table for rapid retrieval of surface approximation information. For example, eight cubically adjacent data points associated with a given voxel element are compared with a predetermined threshold value or range to generate an eight bit vector. This eight-bit vector is employed to rapidly produce vector lists of approximating surfaces. An interpolation operation is performed so as to more closely approximate the desired surface and to provide more accurate representations of vectors normal to the desired surface. The accurate representation of these normal directions provides means for accurately representing shading information on a display screen. U.S. Pat. No. 4,710,876, entitled "System and Method for the Display of Surface Structures Contained within the Interior Region of a Solid Body," provides further details and is incorporated herein by reference The software for producing the display of the virtual environment 185 includes a portion for generating surfaces when the user moves the simulated medical device to create a tunnel within the simulated patient, Such a simulated medical device can be, for example, the simulated dissector device for the MIVH procedure, or any other type of simulated device that produces a tunnel or other cavity within simulated anatomy. In other words, the algorithm described above to generate polygonal surfaces can be used to generate those surfaces when a tool such as a simulated dissector device cuts through the volume to produce a tunnel.

Figure 16:
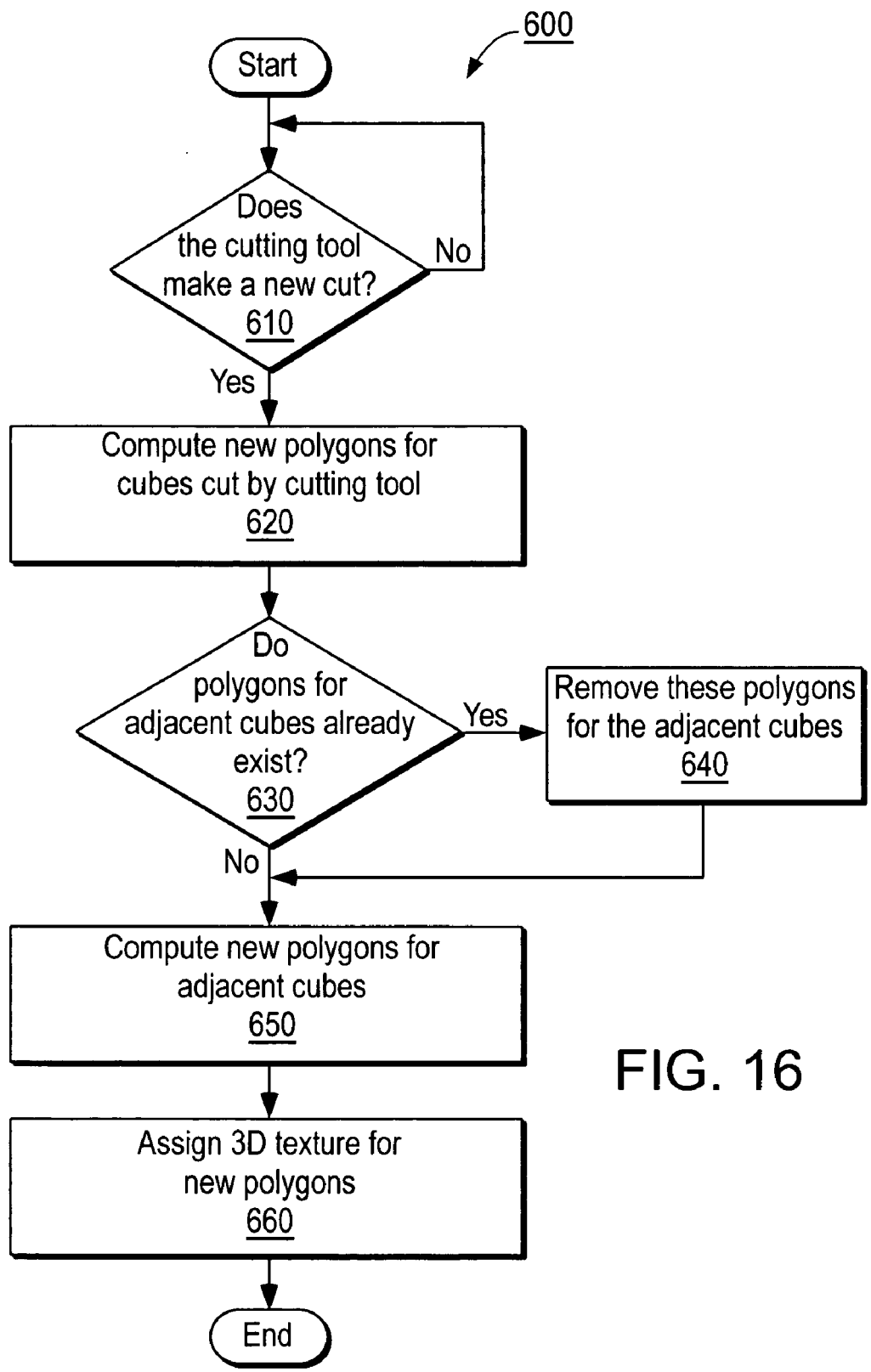
FIG. 16 is a flow chart for generating surfaces within the virtual environment when the user moves the simulated medical device to create a tunnel, according to an embodiment of the invention.

The polygonal surface need not be wholly re-constructed every time that the cutting tool makes a new cut; instead, the implicit surface can be used to grow the tunnel. The cutting tool can be, for example, both deform and cut the cubes. FIG. 16 is a flow chart for generating surfaces within the virtual environment when the user moves the simulated medical device to create a tunnel, according to an embodiment of the invention.

As shown in FIG. 16, at conditional step 610, a determination is made as to whether the cutting tool makes a new cut within the virtual environment. When the cutting tool makes a new cut, only the surface passing through cubes adjacent to the cutting-tip needs to be recomputed. Thus, at steps 620, 630 and 640, new polygons can be computed for these cubes and their direct adjacent cubes based on the implicit surface function used to represent the cutting tip. In other words, at step 620, new polygons for cubes cut by the cutting tool are computed. At condition step 630, a determination is made as to whether polygons for adjacent cubes already exist. If polygons on the direct adjacent cubes already exist, those polygons are first removed to make room for the new polygons at step 640. At step 650, new polygons for the adjacent cubes are computed. Polygons on all other cubes remain the same during the cutting operation. As new triangles are created by the cutting operation, texture coordinates are assigned from a 3D texture derived from medical cryosection data (visible human) at step 660 to give the displayed surface a realistic appearance.

The cubic volume can be deformed through either geometric or physical algorithms. Using geometric deformation, each cube can be deformed to move in the direction of the nearest point on the inserted (i.e., virtual) cutting tool, with a magnitude inversely proportional to its distance from the scope. Alternatively, applying a physical algorithm to the same system, each point in the cube can, for example, be modeled as a particle in a particle system. The particles can then be repelled by the inserted (polygonal) scope model, and through an iterative process, neighbors connected by springs to the displaced particles are moved as well.

Simulation system 100 is particularly well suited to simulate a medical procedure, such as the MIVH procedure, that involves a medical device used in conjunction with palpation by the medical practitioner. In the case of the MIVH procedure, movement of the dissector device and the electrocautery device is highly constrained, particularly at long insertion distances within the patient's leg. Consequently, the medical practitioner uses the free hand to deform the tissue in front of the device tip so as to steer the tissue onto the tip of the dissector device or to the capture portion of the electrocautery device.

In other embodiments, a simulation system can be configured to simulate other procedures including medical procedures such as, for example, a colonoscopy and setting a broken or fractured femur bone. More specifically, other embodiments can be configured to simulate a colonoscopy procedure where the user moves a medical device (or simulated medical device) with one hand and palpates the simulated patient's bowels with the other hand. In such an embodiment, the virtual environment can be configured to simluate the view of an endoscopic device in coordination with the user's movements of the manipulandum and the palpation region of the housing.

Figure 14:
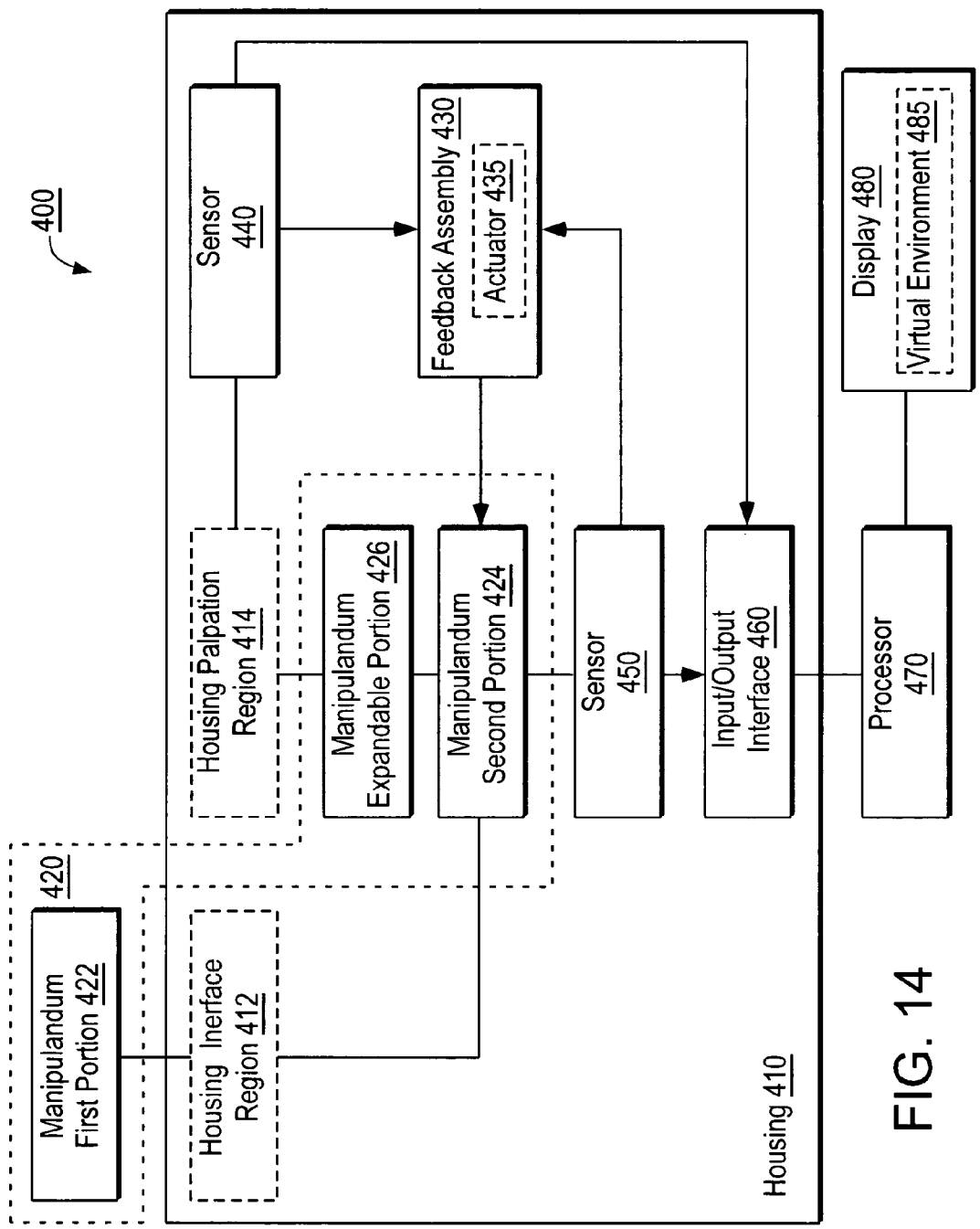
FIG. 14 shows a system block diagram of simulation system having a palpation region, according to another embodiment of the invention.

Similarly, other embodiments can be configured to simulate a procedure for setting a broken or fractured femur bone. In these embodiments, a manipulandum or simulated medical device is not present and, instead, the user palpates one palpation region with one hand and palpates a different palpation region with the other hand. In such embodiments, haptic feedback can be output separately to the two palpation regions. In addition, the user's movement of one palpation region can affect the other palpation region, either directly or through the combination of a sensor to measure the palpation and an actuator at the other palpation region to output the haptic feedback. In such embodiments, the virtual environment and display need not be present; alternatively, the virtual environment and display can be included to provide the user with a view of the effect the user's palpation has on internal anatomical structures FIG. 14 shows a system block diagram of simulation system having a palpation region, according to another embodiment of the invention. As shown in FIG. 14, simulation system 400 includes housing 410, manipulandum 420, feedback assembly 430, sensors 440 and 450, input/output interface 460, processor 470 and display 480. Housing 410 includes housing interface region 412 and housing palpation region 414. Manipulandum 420 includes manipulandum first portion 422, manipulandum second portion 424 and manipulandum expandable portion 426. Feedback assembly 430 includes an actuator 435. Display 480 includes virtual environment 485. In this embodiment, feedback assembly 430, sensors 440 and 450, and input/output interface 460 are disposed within housing 410.

In this embodiment, the manipulandum first portion 422 can be external to housing 410, and manipulandum second portion 424 and manipulandum expandable portion 426 can be internal to housing 410. Manipulandum first portion 422 and manipulandum second portion 424 can be, for example, monolithically formed, integrally formed or removably formed.

In this embodiment, manipulandum expandable portion 426 can have, for example, an adjustable size that maintains an end portion of manipulandum second portion 424 in physical contact with palpation region 414 of housing 410 through manipulandum expandable portion 426. The size of manipulandum expandable portion 426 can be adjusted, for example, through the use of sensor 440 and an actuator such as actuator 435. A movement of manipulandum 420 and/or a palpation of housing palpation region 414 can be detected by sensor 440 and the size of manipulandum expandable portion 426 can be adjusted by the actuator based on a signal output by sensor 440. Manipulandum expandable portion 426 can be, for example, a balloon or bladder that expands when actuated.

By maintaining physical contact between manipulandum 420 and housing palpation region 414, haptic feedback can be conveyed between manipulandum 420 and palpation region 414 and vice versa. For example, when actuator 435 applies haptic feedback to manipulandum second portion 424, the haptic feedback is also conveyed to housing palpation region 414 through manipulandum expandable portion 426. Similarly, when a user palpates housing palpation region 414, the forces associated with this palpation can be conveyed to manipulandum 420 through manipulandum expandable portion 426.

Manipulandum expandable portion 426 can be used in conjunction with feedback assembly 435 or in lieu of feedback assembly 435. In other words, in some embodiments, manipulandum expandable portion 426 can be used to complement the haptic feedback provided to manipulandum second portion 424 by feedback assembly 430. In other embodiments, manipulandum expandable portion 426 can provide the haptic feedback solely such that feedback assembly 430 is not present. In such embodiments, when the manipulandum is moved, the corresponding force at the interior end portion of the manipulandum is translated to the housing palpation region.

In yet other embodiments, manipulandum expandable portion 426 is optional and not present. In such embodiments, a second feedback assembly (not shown) having its own actuator can provide haptic feedback to the housing palpation region 414. In other words, feedback assembly 435 can provide haptic feedback to manipulandum second portion 424 and the second feedback assembly can separately provide haptic feedback to the housing palpation region 414.

Although examples of the palpation region of the housing have been described above as a deformable membrane to which a sensor is coupled to detect movement, other materials and configurations are possible. For example, the housing palpation region can be formed of a deformable material or structure that can be actuated without an intervening actuator between the housing palpation region and the manipulandum. Such a deformable material can be, for example, a shape memory alloy; such a deformable structure can be, for example, a tensile erect surface or a collection of interconnected tensor members. These deformable materials or structures can actuate the housing palpation region, for example, in direct response to movement of the manipulandum.

CONCLUSION

While various embodiments of the invention have been described above, it should be understood that they have been presented by way of example only, and not limitation. Thus, the breadth and scope of the invention should not be limited by any of the above-described embodiment examples, but should be defined only in accordance with the following claims and their equivalents.

While the invention has been particularly shown and described with reference to embodiments thereof, it will be understood by those skilled in the art that various changes in form and details may be made therein without departing from the spirit and scope of the invention.

What is claimed is:

1. An apparatus, comprising:
   a manipulandum;

a housing having a palpation region to be palpated, the palpation region of the housing being spaced apart from the manipulandum;

a first sensor coupled to the palpation region of the housing, the sensor configured to send a signal based on a palpation of the palpation region of the housing;

a second sensor coupled to the manipulandum, the second sensor configured to send a signal based on a position of the manipulandum; and an actuator coupled to the manipulandum, the actuator configured to send haptic output to the manipulandum based on the signal from the first sensor and the signal from the second sensor.

2. The apparatus of claim 1, wherein the manipulandum includes a first portion and a second portion, the first portion of the manipulandum being disposed within an interaction region of the housing different from the palpation region of the housing, the second portion of the manipulandum being coupled to the palpation region of the manipulandum.

3. The apparatus of claim 1, the manipulandum being a simulated medical device, the palpation region of the housing being a simulated tissue, the apparatus further comprising:

a processor configured to provide signals associated with display of a virtual environment, the signals associated with the virtual environment being based on a position of the simulated medical device and the signal from the sensor associated with the palpation of the simulated tissue.

4. The apparatus of claim 1, wherein:

the manipulandum includes a first portion and a second portion, the first portion of the manipulandum being disposed within an interaction region of the housing different from the palpation region of the housing, the second portion of the manipulandum being coupled to the palpation region of the housing, the second portion of the manipulandum having an expandable portion configured to contact directly the palpation region of the housing.

5. The apparatus of claim 1, wherein:

the manipulandum has a first configuration and a second configuration different from the first configuration, the first configuration of the manipulandum configured to simulate a dissector endoscope device associated with a vein harvesting medical procedure, the second configuration of the manipulandum configured to simulate an electrocautery endoscope device associated with the vein harvesting medical procedure.

6. An apparatus, comprising:

a manipulandum;

a housing having a palpation region to be palpated, the palpation region of the housing being spaced apart from the manipulandum;

a sensor coupled to the palpation region of the housing, the sensor configured to send a signal based on a palpation of the palpation region of the housing; and an actuator coupled to the manipulandum, the actuator configured to send haptic output to the manipulandum based on the signal, wherein the manipulandum is a simulated medical device, the palpation region of the housing is a simulated tissue, and the apparatus further comprises:

a processor configured to provide signals associated with display of a virtual environment, the signals associated with the virtual environment being based on a position of the simulated medical device and the signal from the sensor associated with the palpation of the simulated tissue, the virtual environment having an interior view of a virtual body portion associated with the simulated tissue, the virtual environment including a virtual medical device and the virtual body portion, movement of the virtual medical device being based on movement of the simulated medical device, movement of the virtual body portion being based on palpation of the simulated tissue.

7. An apparatus, comprising:

a manipulandum;

a housing having a palpation region to be palpated, the palpation region of the housing being spaced apart from the manipulandum;

a sensor coupled to the palpation region of the housing, the sensor configured to send a signal based on a palpation of the palpation region of the housing; and an actuator coupled to the manipulandum, the actuator configured to send haptic output to the manipulandum based on the signal, wherein the manipulandum is a simulated medical device, the palpation region of the housing is a simulated tissue, and the apparatus further comprises:

a processor configured to provide signals associated with display of a virtual environment, the signals associated with the virtual environment being based on a position of the simulated medical device and the signal from the sensor associated with the palpation of the simulated tissue, the virtual environment having an interior view of a virtual body portion associated with the simulated tissue, the virtual environment including a virtual medical device and the virtual body portion, movement of the virtual medical device and movement of the virtual body portion being based on movement of the simulated medical device and palpation of the simulated tissue.

8. An apparatus, comprising:

a housing having a palpation region to be palpated and an interface region different from the palpation region;

a manipulandum having a first portion and a second portion, the first portion of the manipulandum coupled to the interface region of the housing, the second portion of the manipulandum being spaced apart from the palpation region of the housing and being moveable such that a force is translated to the palpation region of the housing when the manipulandum is moved; and an actuator coupled to the manipulandum, the actuator configured to send haptic output to the manipulandum, wherein the manipulandum is a simulated medical device, the palpation region of the housing is a simulated tissue, and the apparatus further comprises:

a first sensor coupled to the palpation region of the simulated tissue, the sensor configured to send a signal based on a palpation of the simulated tissue; and a processor configured to provide signals associated with display of a virtual environment, the signals associated with the virtual environment being based on a position of the simulated medical device and the signal from the sensor associated with the palpation of the simulated tissue.

9. The apparatus of claim 8, further comprising:

a second sensor coupled to the manipulandum, the second sensor configured to send a signal based on a position of the manipulandum, and the actuator configured to send the haptic output to the manipulandum based on the signal from the first sensor and the signal from the second sensor.

10. The apparatus of claim 8, the actuator being a first actuator, the apparatus further comprising:
- a second sensor coupled to the manipulandum, the second sensor configured to send a signal based on a position of the second portion of the manipulandum; and
- a second actuator coupled to the palpation region of the housing, the second actuator configured to send haptic output to the palpation region of the housing based on the signal.

11. The apparatus of claim 8, wherein:
the second portion of the manipulandum has an expandable portion configured to contact directly the palpation region of the housing.

12. The apparatus of claim 8, wherein the virtual environment has an interior view of a virtual body portion associated with the simulated tissue, the virtual environment includes a virtual medical device and the virtual body portion, movement of the virtual medical device is based on movement of the simulated medical device, and movement of the virtual body portion is based on palpation of the simulated tissue.

13. The apparatus of claim 8, wherein the virtual environment has an interior view of a virtual body portion associated with the simulated tissue, the virtual environment includes a virtual medical device and the virtual body portion, and movement of the virtual medical device and movement of the virtual body portion are being based on movement of the simulated medical device and palpation of the simulated tissue.

14. The apparatus of claim 8, wherein:
the manipulandum has a first configuration and a second configuration different from the first configuration,
the first configuration of the manipulandum configured to simulate a dissector endoscope device associated with a vein harvesting medical procedure,
the second configuration of the manipulandum configured to simulate an electrocautery endoscope device associated with the vein harvesting medical procedure.

15. A method, comprising:
receiving a first signal associated with a position of a manipulandum disposed within an interface region of a housing, the housing having a palpation region to be palpated the palpation region different from the interface region;
receiving a second signal associated with a palpation of the palpation region of the housing;
sending a third signal to a first actuator coupled to the manipulandum based on the first signal and the second signal, the actuator configured to send a haptic force to the manipulandum based on the third signal; and
sending a signal to a second actuator coupled to the palpation region of the housing based on the first signal, the second actuator configured to send a haptic force to the manipulandum based on the signal sent to the second actuator.

16. The method of claim 15, further comprising:
sending signals associated with display of a virtual environment based on the first signal and the second signal.

17. A method, comprising:
receiving a first signal associated with a position of a manipulandum disposed within an interface region of a housing, the housing having a palpation region to be palpated the palpation region different from the interface region;
receiving a second signal associated with a palpation of the palpation region of the housing; and
sending a third signal to an actuator coupled to the manipulandum based on the first signal and the second signal, the actuator configured to send a haptic force to the manipulandum based on the third signal,
wherein the manipulandum being a simulated medical device, the housing being a simulated tissue, the method further comprising:
sending signals associated with display of a virtual environment based on the first signal and the second signal such that the virtual environment has an interior view of a virtual body portion associated with the simulated tissue, the virtual environment including a virtual medical device and the virtual body portion, movement of the virtual medical device being based on the first signal, movement of the virtual body portion being based on the second signal.

* * * * *